US009290738B2

(12) United States Patent
Ross et al.

(10) Patent No.: US 9,290,738 B2
(45) Date of Patent: Mar. 22, 2016

(54) METHODS OF DECELLULARIZING BONE (71) Applicant: Miromatrix Medical Inc., Eden Prairie, MN (US)

(72) Inventors: Jeffrey Ross, Chaska, MN (US); Blaise Porter, Eden Prairie, MN (US)

(73) Assignee: Miromatrix Medical Inc., Eden Prairie, MN (US)

( * ) Notice: Subject to any disclaimer, the term of this patent is extended or adjusted under 35 U.S.C. 154(b) by 0 days.

(21) Appl. No.: 13/787,625

(22) Filed: Mar. 6, 2013

(65) Prior Publication Data
US 2013/0337560 A1 Dec. 19, 2013

Related U.S. Application Data (60) Provisional application No. 61/659,046, filed on Jun. 13, 2012.

(51) Int. Cl.
C12N 5/071 (2010.01)
A61F 2/28 (2006.01)
C12N 5/077 (2010.01)
A61F 2/46 (2006.01)

(52) U.S. Cl.
CPC ............ *C12N 5/0654* (2013.01); *A61F 2/4644* (2013.01); *A61F 2002/4646* (2013.01)

(58) Field of Classification Search
None
See application file for complete search history.

(56) References Cited

U.S. PATENT DOCUMENTS

| | | | |
|---|---|---|---|
| 3,545,221 A | 12/1970 | Koski et al. | |
| 3,639,084 A | 2/1972 | Goldhaber | |
| 4,083,066 A | 4/1978 | Schmitz et al. | |
| 4,801,299 A | 1/1989 | Brendel et al. | |
| 5,336,616 A | 8/1994 | Livesey et al. | |
| 5,820,581 A * | 10/1998 | Wolfinbarger, Jr. | ........... 604/500 |
| 6,376,244 B1 | 4/2002 | Atala | |
| 6,379,963 B2 | 4/2002 | Haverich et al. | |
| 6,416,995 B1 | 7/2002 | Wolfinbarger | |
| 6,432,712 B1 | 8/2002 | Wolfinbarger, Jr. | |
| 6,479,064 B1 | 11/2002 | Atala | |
| 6,689,161 B2 | 2/2004 | Chen et al. | |
| 6,749,064 B1 | 6/2004 | Alrey | |
| 6,753,181 B2 | 6/2004 | Atala et al. | |
| 6,960,427 B2 | 11/2005 | Haverich et al. | |
| 6,962,814 B2 | 11/2005 | Mitchell et al. | |
| 7,311,904 B2 | 12/2007 | Hariri | |
| 7,354,749 B2 | 4/2008 | Fisher et al. | |
| 8,470,520 B2 | 6/2013 | Ott et al. | |
| 2001/0049138 A1 | 12/2001 | Dennis et al. | |
| 2002/0081728 A1 | 6/2002 | Haverich et al. | |
| 2003/0087428 A1 | 5/2003 | Wolfinbarger, Jr. et al. | |
| 2003/0096407 A1 | 5/2003 | Atala et al. | |
| 2003/0124099 A1 | 7/2003 | Atala et al. | |
| 2003/0215945 A1 | 11/2003 | Atala | |
| 2004/0176855 A1 | 9/2004 | Badylak | |
| 2004/0187877 A1 | 9/2004 | Badylak et al. | |
| 2005/0084512 A1 | 4/2005 | Denizeau et al. | |
| 2005/0249816 A1 | 11/2005 | Atala et al. | |
| 2007/0059293 A1 | 3/2007 | Atala | |
| 2008/0058956 A1 | 3/2008 | Badylak | |
| 2009/0169525 A1 | 7/2009 | Anversa et al. | |
| 2009/0202977 A1 | 8/2009 | Ott et al. | |
| 2011/0059152 A1 | 3/2011 | Atala | |
| 2012/0183944 A1 | 7/2012 | Taylor et al. | |
| 2013/0109088 A1 | 5/2013 | Ott et al. | |
| 2013/0156744 A1 | 6/2013 | Taylor et al. | |
| 2013/0344599 A1 | 12/2013 | Ott et al. | |

FOREIGN PATENT DOCUMENTS

| | | |
|---|---|---|
| CN | 1615162 A | 5/2005 |
| CN | 101066477 A | 11/2007 |
| CN | 101272815 A | 9/2008 |
| EP | 1246903 A1 | 1/2008 |
| EP | 2431063 A2 | 3/2012 |
| EP | 1928519 B1 | 4/2012 |
| JP | 55-016016 A | 4/1980 |
| JP | 06-261933 A | 9/1994 |
| JP | 2004-167236 A | 6/2004 |
| JP | 2005-509495 A | 4/2005 |
| JP | 2009-505752 A | 2/2009 |
| WO | WO-96/08213 A1 | 3/1996 |
| WO | WO-01/48153 A1 | 7/2001 |
| WO | WO-01/49210 A1 | 7/2001 |
| WO | WO-02/24244 A2 | 3/2002 |
| WO | WO-02/40630 A2 | 5/2002 |
| WO | WO-02/49681 A1 | 6/2002 |
| WO | WO-02/063962 A1 | 8/2002 |
| WO | WO-03/039610 A1 | 5/2003 |
| WO | WO-03/043674 A1 | 5/2003 |
| WO | WO-2004/054571 A1 | 7/2004 |
| WO | WO-2004/080501 A1 | 9/2004 |

(Continued)

OTHER PUBLICATIONS

Frohlich, M., Grayson, W.L., Wan, L.Q., Marolt, D., Drobnic, M., and Vunjak-Novakovic, G. "Tissue engineered bone grafts: biological requirements, tissue culture and clinical relevance", Current Stem Cell Research & Therapy 2008, vol. 3, pp. 254-264.*
International Application Serial No. PCT/US2013/045387, International Search Report mailed Oct. 10, 2013, 4 pgs.
International Application Serial No. PCT/US2013/045387, Written Opinion mailed Oct. 10, 2013, 5 pgs.
Grayson, Warren L, et al., "Effects of Initial Seeding Density and Fluid Perfusion Rate on Formation of Tissue-Engineered Bone", Tissue Engineering: Part A, vol. 14, No. 11, (Nov. 1, 2008), 1809-1820.
Hashimoto, Yoshihide, et al., "The effect of decellularized bone/bone marrow produced by high-hydrostatic pressurization on the osteogenic differentiation of mesenchymal stem cells", Biomaterials, vol. 32, No. 29, (Oct. 2011), 7060-7067.
Atala, A., "Recent developments in tissue engineering and regenerative medicine", *Curr. Opin. Pediatr.*, 18(2), (2006), 167-171.
Atala, A., et al., "Tissue-engineered autologous bladders for patients needing cystoplasty", *Lancet*, 367(9518), (2006), 1241-1246.
Bader, A., et al., "Tissue engineering of heart valves—human endothelial cell seeding of detergent acellularized porcine valves", *Eur. J. Cardiothorac. Surg*, 14(3), (1998), 279-284.
Badylak, S. F., et al., "Whole-organ tissue engineering: decelluarization and recellualarization of three-dimensional matrix scaffolds.", *Annu Rev Biomed Eng.*, 13, (2011), 27-53.

(Continued)

*Primary Examiner* — Renee Claytor
*Assistant Examiner* — Michelle F Paguio Frising
(74) *Attorney, Agent, or Firm* — Schwegman Lundberg & Woessner, P.A.

(57) ABSTRACT

The invention provides methods for decellularizing bone, e.g., human bone.

21 Claims, 3 Drawing Sheets

(56) References Cited

FOREIGN PATENT DOCUMENTS

| WO | WO-2004/100832 A1 | 11/2004 |
|---|---|---|
| WO | WO-2005/118014 A2 | 12/2005 |
| WO | WO-2006/033415 A1 | 3/2006 |
| WO | WO-2006/122533 A2 | 11/2006 |
| WO | WO-2007025233 A1 | 3/2007 |
| WO | WO-2010/120539 A1 | 10/2010 |
| WO | WO-2010/120539 A2 | 10/2010 |
| WO | WO-2010/120539 A3 | 2/2011 |
| WO | WO-2011/031484 A2 | 3/2011 |
| WO | WO 2012/031162 A1 | 12/2013 |
| WO | WO-2013/188525 A1 | 12/2013 |

OTHER PUBLICATIONS

Badylak, S. F., "Xenogeneic extracellular matrix as a scaffold for tissue reconstruction", *Transpl. Immunol.*, 12(3-4), (2004), 367-377.

Baetschiger, R. M., et al., "Xenotransplantation Literature Update Nov.-Dec. 2005", *Xenotransblantation*, 13(2), (2006), 96-99.

Baptista, P. M., et al., "A Novel Acellular Biologically Derived Scaffold for Tissue Engineering", Pittsburgh Tissue Engineering Initiative, [retrieved on Jul. 27, 2005] [Online]. Retrieved from the Internet: <URL: www.regenerate-online.com/abstract_Baptista.html>, (2005), 2 pgs.

Baptista, P. M, et al., "Human liver bioengineering using a whole liver decellularized bioscaffold", *Methods Mol Biol.*, 1001, (Abstract Only), (2013), 1 pg.

Baptista, P. M, et al., "The use of whole organ decellularization for the generation of a vascularized liver organoid.", *Hepatology*, 53(2), (Feb. 2011), 604-617.

Baptista, P., et al., "A Novel Whole Organ Bioscaffold for Tissue Engineering and Regenerative Medicine Applications", The FASEB Journal, 21 (Meeting Abstract Supplement). *Database Biosis Abstract*, (2007), A1233.

Bodnar, E., et al., "Damage of Porcine Aortic Valve Tissue Caused by the Surfactant Sodiurndodecylsulphate", *Thorac. Cardiovasc. Surg.*, 34(2), (1986), 82-85.

Bonvillain, R. W, et al., "A nonhuman primate model of lung regeneration: detergent-mediated decellularization and initial in vitro recellularization with mesenchymal stem cells.", *Tissue Eng Part A.*, 18(23-24), (Abstract Only), (Dec. 2012), 1 pg.

Borschel, G. H., et al., "Contractile Skeletal Muscle Tissue-Engineered on an Acellular Scaffold", *Plast.. Reconstr. Surg.*, 113(2), (2004), 595-602.

Brendel, K., et al., "The acellular perfused kidney: a model for basement membrane permeability", *Biology and Chemistry of Basement Membranes*, Nicholas A Kefalides, author; New York : Academic Press, (1978), 177-193.

Cartmell, J. S., et al., "Development of Cell-Seeded Patellar Tendon Allografts for Anterior Cruciate Ligament Reconstruction", *Tissue Eng.*, 10(7-8) (2004), 1065-1075.

Ceboari, S., et al., "Construction of Autologous Human Heart Valves Based on an Acellular Allograft Matrix", *Circulation*,106 (Suppl 1), (2002), 1-63-1-68.

Chen, F., et al., "Acellular collagen matrix as a possible "off the shelf" biomaterial for urethral repair". *Urology*, 54(3), (1999), 407-410.

Chen, F., et al., "Experimental and clinical experience using tissue regeneration for urethral reconstruction", *World J. Urol.*, 18(1), (2000), 67-70.

Chen, R.-Y., et al., "Process development of an acellular dermal matrix (ADM) for biomedical applications", *Biomaterials*, 25, (2004), 2679-2686.

Conconi, M. T., et al., "Homologous muscle acellular matrix seeded with autologous myoblasts as a tissue-engineering approach to abdominal wall-defect repair", *Biomaterials*, 26(15), (2005), 2567-2574.

Courtman, D. W., et al., "Development of a pericardial acellular matrix biomaterial: Biochemical and mechanical effects of cell extraction", *J Biomed Materi Res.*, 28(6), (1994).

Crapo, P. M.., et al., "An overview of tissue and whole organ decellularization process", *Biomaterials*, 32, (2011), 3233-3243.

Dahl, S. L. et al., "Decellularized Native and Engineered Arterial Scaffolds for Transplantation", *Cell Transplant.*, 12(6) (2003), 659-666.

Daly, A. B, et al., "Initial binding and recellularization of decellularized mouse lung scaffolds with bone marrow-derived mesenchymal stromal cells", *Tissue Eng Part A.*, 18(1-2), (Abstract Only), (Jan. 2012), 1 pg.

Davis, G. E., et al., "Endothelial Extracellular Matrix—Biosynthesis, Remodeling, and Functions During Vascular Morphogenesis and Neovessel Stabilization", *Circ. Res.*,. 97, (2005), 1093-1107.

Dellgren, G., et al., "Eleven years' experience with the Biocor stentless aortic bioprsthesis: clinical and hemodynamic follow-up with long-term relative survival rate", Eur. *J. Cardiothorac., Surg.*, 22(6), (2002), 912-921.

Den Butter, G., et al., "Comparison of solutions for preservation of the rabbit liver as tested by isolated perfusion", *Transpl.. Int.*, 8(6), (1995), 466-471.

Deng, M. C., et al., "Destination Mechanical circulatory Support: Proposal for Clinical Standards", *J. Heart Lung Transplant.*, 22(4), (2003), 365-369.

Deyl, Z., et al., "Steric Hindrances in Protein Permeation Through the Basement Membrane Studied in Acellular Kidney", *Physiologia Bohemoslovaca*, 36(5), (1987), 425-434.

Elkins, R. C., et al., "Decellularized Human Valve Allografts", *Ann. Thorac. Surg.*, 71(Suppl 5), (2001), S428-S432.

Engbers-Buijtenhuijs, P., et al., "Biological characterisation of vascular grafts cultured in a bioreactor", *Biomaterials*, 27(11), (2006), 2390-2397.

Eshenhagen, T., et al., "Engineering Myocardial Tissue", *Circ. Res.*, 97(12), (2005), 1220-1231.

Faulk, D. M., et al., "Role of the Extracellular Matrix in Whole Organ Engineering", *J Cell Physiol.*, (Abstract Only), (Dec. 18, 2013), 1 pg.

Firth, J. D., et al., "Sodium handling in the isolated perfused kidney of the cirrhotic rat", *Clin, Sci.*, 77(6), (1989), 657-661.

Furuta, A., et al., "Pulsatile Cardiac Tissue Grafts Using a Novel Three-Dimensional Cell Sheet Manipulation Technique Functionally Integrates With the Host Heart, in Vivo", *Circ. Res*,. 98(5), (2006), 705-712.

Gerecht-Nir, S., et al., "Biophysical regulation during cardiac development and application to tissue engineering", *Int. J. Dev. Biol.*, 50(2-3), (2006), 233-243.

Gilbert, T. W., et al., "Decellularization of tissues and organs", *Biomaterials*, 27, (2006), 3675-3683.

Grabow, N., et al., "Mechanical and Structural Properties of a Novel hybrid heart Valve Scaffold for Tissue Engineering", *Artif. Organs*, 28(11), (2004), 971-979.

Groetzner, J., et al., "Results of Pediatric Cardiac Transplantation—Long-Term Results of a 15-Year Experience", *Thorac. Cardiov. Surg.*, 53 (Suppl 2), (2005), S149-S154.

Hohlfeld, J., et al., "Tissue engineered fetal skin constructs for paediatric burns", *Lancet*, 366(8488), (2005), 840-842.

Hopper, R. A., et al., "Acellulatization of Human Placenta With Preservation of the Basement Membrane", *Ann. Plast. Surg.*, 51, (2003), 598-602.

Hou, S.-Y., et al., "Tissue-engineered peripheral nerve grafting by differentiated bone marrow stromal cells", *Neuroscience*, 140(1), (2006), 101-110.

Hudson, T. W., et al., "Engineering an Improved Acellular Nerve Graft via Optimized Chemical Processing", *Tissue Eng.*, 10(9-10), (2004), 1346-1358.

Ikeda, E., et al., "Growing bioengineered teeth from single cells: potential for dental regenerative medicine", *Expert Opin. Biol. Ther*, 8(6), (2008), 735-744.

Isenberg, B. C., et al., "Small Diameter Artificial Arteries Engineered In Vitro", *Circ. Res.*, 98(1), (2006), 25-35.

Jawad, H., et al., "Myocardial tissue engineering", *British Medical Bulletin*, 87, (2008), 31-47.

Juncosa-Melvin, N., et al., "The Effect of Autologous Mesenchymal Stem Cells on the Biomechanics and Histology of Gel-Collagen Sponge Constructs Used for Rabbit Patellar Tendon Repair", *Tissue Eng.*, 12(2), (2006), 369-379.

(56) References Cited

OTHER PUBLICATIONS

Kasimir, M.-T., et al., "The decellularized porcine heart valve matrix in tissue engineering. Platelet adhesion and activation", *Thromb. Haemost.*, 94, (2005), 562-567.

Ketchedjian, A., et al., "Recellularization of Decellularized Allograft Scaffolds in Ovine Great Vessel Reconstructions", *Ann. Thorac. Surg.*, 79(3), (2005), 888-896.

Knight, R. L., et al., "Tissue Engineering of Cardiac Valves: Re-Seeding of Acellular Porcine Aortic Valve Matrices with human Mesenchymal Progenitor Cells", *J. Heart Valve Dis.*, 14(6), (2005), 806-813.

Kofidis, T., et al., "Myocardial Restoration and Tissue Engineering of Heart Structures", *Methods Mol. Med.*, 140, (2007), 273-290.

Kolker, A. R., et al,, "Multilayer Reconstruction of abdominal Wall defects with Acellular Dermal Allograft (AlloDerm) and component Separation", *Ann. Plast. Surg.*, 55(1), (2005), 36-41.

Kren. S., et al., "The Production of a Bio-Engineered Endothelial Intima From Cultured Cells Using Whole Cardiac Cadaveric Extracellular Matrix". *Circulation*, 116 (Meeting Abstract Supplement), Database Biosis, (2007), 4 pgs.

Langer, R., et al., "Tissue Engineering", *Science*, 260, (1993), 920-926.

Lee, M. S., "GraftJacket Augmentation of Chronic Achilles Tendon Ruptures", *Orthopedics*, 27(1 Suppl.), (2004), 151-153.

Levenberg, S., et al., "Engineering vascularized skeletal muscle tissue", *Nat. Biotechnol.*, 23(7), (2005), 879-884.

L'Heureux, N., et al., "Human tissue-engineered blood vessels for adult arterial revascularization", *Nat. Med.*, 12(3), (2006), 361-365.

Lichtenberg, A., et al., "Flow-Dependent Re-Endothelialization of Tissue-Engineered Heart Valve", *J. Heart Valve Dis.*, 15(2), (2006), 287-294.

Lin, P., et al., "Accessing Porcine Liver-Derived Biornatrix for Hepatic Tissue Engineering", *Tissue Eng.*, 10(7-8), (2004), 1046-1053.

Matsuura, J. H., et al., "Cellular Remodeling of Depopulated Bovine Ureter Used as an Arteriovenous Graft in the Canine Model", *J. Am. Coll. Surg.*, 198(5), (2004), 778-783.

Matthiesen, T. S., et al., "Abstract 572: Large Solid Organ Perfusion Decellularization—A Start for Human-Sized Tissue Scaffolds", *Circulation*, 116 Suppl. S,, (2007), 1 pg.

Matthiesen, T., et al., "Creating Biocornpatible 3-D Scaffolds for Engineering Cardiovascular Tissues: Heart, Lung, and Kidney", *Circulation*, 116 (Meeting Abstract Supplement), Database Biosis, (Oct. 2007), 4 pgs.

Matthiesen, T. S., et al., "Large Solid Organ Perfusion Decellularization—A Start for Huamn-Sized Tissue Scaffolds?", *Circulation*, 116 (Meeting Abstract Supplement), Database Biosis, (Oct. 2007), 4 pgs.

Mazzetti, S., et al., "Molecular anatomy of the cerebral microvessels in the isolated guinea-pig brain", *Brain Res.*, 999(1), (2004), 81-90.

McFetridge, P. S., et al., "Preparation of porcine carotid arteries for vascular tissue engineering applications", *J. Biomed. Mater Res. A*, 70(2), (2004), 224-234.

Mirsadraee, S., et al., "Development and Characterization of an Acellular Human Pericardial matrix for Tissue Engineering", *Tissue Eng.*, 12(4), (2006), 763-773.

Miyagawa, S., et al., "Tissue Cardiomyoplasty using bioengineered Contractile Cardiomyocyte Sheets to Repair Damaged Myocardium: Their Integration with Recipient Myocardium", *Transplantation*, 80(11), (2005), 1586-1595.

Nikalson, L. E., et al., "Functional Arteries Grown in Vitro", *Science*, 284(5413), (1999), 489-493.

Oliver, R. F., et al., "Dermal collagen Implants", Biomaterials, 3(1), (1982), 38-40.

Ott, H. C. et al., "Cell-Based Cardiovascular Repair", *Basic Res Cardiol*, 100, (2005), 504-517.

Ott, H. C, et al., "Perfusion-Decellularized Matrix: Using Nature's Platform to Engineer A Bioartificial Heart", *Nat. Med.*, 14(2), (Abstract Only), (2008), 1 pg.

Ott, H. C, et al., "Perfusion-decellularized matrix: using nature's platform to engineer a bioartificial heart", *Nat Med.*, 14(2), (Feb. 1, 2008), 213-221.

Ott, H. C, et al., "Regeneration and orthotopic transplantation of a bioartificial lung", *Nat Med.*, 16(8), (Abstract Only), (Aug. 2008), 1 pg.

Ott, H. C, et al., "Regeneration and orthotopic transplantation of a bioartificial lung", *Nature Medicine*, Advance Online Publication, (2010), 8 pgs.

Park, H., et al., "A novel composite scaffold for cardiac tissue engineering", *In Vitro Cell Dev. Biol. Anim.*, 41, (2005), 188-196.

Pelham, Jr., et al., "Cell locomotion and focal adhesions are regulated by substrate flexibility", *Proc. Natl. Acad. Sci. USA 94*, (1997), 13661-13665.

Peters, J. M., et al., "Organ Weights and Water Levels of the Rat following Reduced Food Intake", *The Journal of Nutrition*, 90, (1966), 354-360.

Petersen, T. H, et al., "Tissue-engineered lungs for in vivo implantation", Science Express, www.scienceexpress.org, (Jun. 24, 2010), 10 pgs.

Petersen, T. H, et al., "Tissue-engineered lungs for in vivo implantation", *Science*, 329(5991), (Abstract Only), (Jul. 30, 2010), 1 pg.

Phillips, J. B., et al., "Neural Tissue Engineering: A Self-Organizing Collagen Guidance Conduit", *Tissue Eng.*, 11, (2005), 1611-1617.

Powers, M. J., et al., "Functional Behavior of Primary Rat Liver Cells in a Three-Dimensional Perfused Microarray Bioreactor", *Tissue Eng.*, 8(3), (2002), 499-513.

Radisic, M., et al., "Mathematical model of oxygen distribution in engineered cardiac tissue with parallel channel array perfused with culture medium containing oxygen carriers.", *Am J Physiol Heart Circ Physiol.*, 288(3), (Mar. 2005), H1278-89.

Rieder, E., et al., "Decellularization protocols of porcine heart valves differ importantly in efficiency of cell removal and susceptibility of the matrix to recellularization with human vascular cells.", *J Thorac Cardiovasc Surg.*, 127(2), (Feb. 2004), 399-405.

Robinson, K. A., et al., "Extracellular Matrix Scaffold for Cardiac Repair", *Circulation 112*[suppl I), (2005), I-135-I-143.

Roy, S., et al., "Biomechanical properties of decellularlzed porcine common carotid arteries", *Am. J. Physiol. Heart Circ. Physiol.*, 289(4), (2005), H1567-H1576.

Sayk, F., et al., "Histopathologic Findings in a Novel Decellularized Pulmonary Homograft: An Autopsy Study", *Ann. Thorac.. Surg.*, 79(5), (2005), 1755-1758.

Schaner, P. J, et al., "Decellularized vein as a potential scaffold for vascular tissue engineering", *J Vasc Surg.*, 40(1), (Jul. 2004), 146-153.

Schenke-Layland, K., et al., "Complete dynamic repopulation of decellularized heart valves by application of defined physical signals-an in vitro study", *Cardiovasc Res.*, 60(3), (Dec. 1, 2003), 497-509.

Schenke-Layland, K., et al., "Impact of decellularlzation of xenogeneic tissue on extracellular matrix integrity for tissue engineering of heart valves", *J. Struct. Biol.*, 143, (2003), 201-208.

Schlager, G., "Kidney Weight in Mice: Strain Differences and Genetic Determinatino", *The Journal of Heredity*, 59, (1968), 171-174.

Schmidt, C. E, et al., "Acellular vascular tissues: natural biomaterials for tissue repair and tissue engineering", *Biomaterials*, 21(22), (Nov. 2000), 2215-31.

Sekine, H., et al., "Cardiornyacyte Bridging Between Hearts and Bioengineered Myocardial Tissues with Mesenchymal Transition of Mesothelial Cells", *J. Heart Lung Transplant.*, 25(3), (2006), 324-332.

Shimizu, T., et al., "Fabrication of pulsatile cardiac tissue grafts using a novel 3-dimensional cell sheet manipulation technique and temperature-responsive cell culture surfaces.", *Circ Res.*, 90(3), (Feb. 22, 2002), e40-e48.

Shyy, J. Y.-J., et al., "Role of Integrins in Endothelial Mechanosensing of Shear Stress", *Circ. Res.*, 91, (2002), 769-775.

Song, J. J, et al., "Regeneration and experimental orthotopic transplantation of a bioengineered kidney", *Nat Med.*, 19(5), (May 2013), 646-51.

Stevenson, L. W., et al., "Left Ventricular Assist Device as Destination for Patients Undergoing Intravenous Inotropic Therapy. A Sub- (56) References Cited

OTHER PUBLICATIONS set Analysis from REMATCH (Randomized Evaluation of Mechanical Assistance in Treatment of Chronic Heart Failure)", *Circulation*, 110(8), (2004), 975-981.

Sudo, R., et al., "Reconstruction of 3d stacked-up structures by rat small hepatocytes on microporous membranes", *FASEB J.*, 19, (2005), 1695-1697.

Sun, T., et al., "Development of a Closed Bioreactor System for Culture of Tissue-Engineered Skin at an Air-Liquid Interface", *Tissue Eng.*, 11(11/12), (2005), 1824-1831.

Takagi, K., et al., "In Vivo Recellularization of Plain Decellularized Xenografts with Specific Cell Characterization in the Systemic Circulation: Histological and Immunohistochemical Study", *Artif. Organs*, 30(4), (2006), 233-241.

Taylor, D. A. et al., "Regenerating Functional Myocardium: Improved Performance after Skeletal Myoblast Transplantation", *Nature Medicine*, 4(8), (1998), 929-933.

Teebken, O. E., et al., "Tissue engineering of vascular grafts: human cell seeding of decellularised porcine matrix", *Eur. J. Vasc. Endovasc. Surg.*, 19(4), (2000), 381-386.

Teebken, O. E, et al., "Tissue engineering:in vitro creation of tissue substitutes", (w/ English Abstract), *Zentralbl Chir.*, 132(3), (2007), 236-246.

Toni, R., et al., "The Bioartifical Thyroid: a Biotechnical Perspective in Endocrine Organ Engineering for Transplantation Replacement", *Acta Biomed.*, 78(Suppl 1), (2007), 129-155.

Uchimura, E., et al., "Novel method of preparing acellular cardiovascular grafts by decellularization with poly(ethylene glycol)", *J. Biomed. Mater. Res.*, 67(3), (2003), 834-837.

Uygun, B. E, et al., "Decellularization and recellularization of whole livers", *J Vis Exp.*, (48), (Abstract Only), (Feb. 2011), 1 pg.

Uygun, Basak E, et al., "Organ reengineering through development of a transplantable recellularized liver graft using decellularized liver matrix". *Nature Medicine*, vol. 16, No. 7, (Jun. 13, 2010), 814-820.

Wagner, S. M., et al., "The isolated normothermic hemoperfused porcine forelimb as a test system for transdermal absoption studies", *J. Artif. Organs*, 6(3), (2003), 183-181.

Walles, T., e al., "Ace Scaffold Implantation—No Alternative to Tissue Engineering", *Int. J. Artif. Organs*, 26(3), (2003), 225-234.

Wang, P.-C., et al., "Reconstruction of Renal Glomerular Tissue Using Collagen Vitrigel Scaffold", *J. Biosci., Bioeng.*, 99(6), (2005) 529-540.

Woods, T., et al., "Effectiveness of three extraction techniques in the development of a decellularized bone-anterior cruciate ligament-bone graft" *Biomaterials*, 26(35), (Dec. 1, 2005), 7339-7349.

Zandonella, C., "Tissue Engineering: The Beat Goes on", *Nature*, 421(6926), (2003), 884-886.

Zeltinger, J., et al., "Development and characterization of Tissue-Engineered Aortic Valves", *Tissue Engineering*, 7(11), (2001), 9-22.

Zimmermann, W. H, et al., "Engineered heart tissue for regeneration of diseased hearts", *Biomaterials*, 25(9), (Apr. 2004), 1639-47.

Zimmermann, W. H, et al., "Engineered heart tissue grafts improve systolic and diastolic function in infarcted rat hearts", *Nat. Med.*, 12(4), (2006), 452-458.

"Chinese Application Serial No. 201380041965.9, Office Action mailed Mar. 19, 2015", 2 pgs.

"International Application Serial No. PCT/US2013/045387, International Preliminary Report on Patentability mailed Dec. 24, 2014", 7 pgs.

U.S. Appl. No. 13/262,286, Final Office Action mailed Jun. 11, 2015, 6 pgs.

U.S. Appl. No. 13/262,286, Non Final Office Action mailed Oct. 9, 2014 , 7 pgs.

U.S. Appl. No. 13/262,286, Response filed Mar. 9, 2015 to Non Final Office Action mailed Oct. 9, 2014, 7 pgs.

U.S. Appl. No. 13/725,030, Advisory Action mailed Jun. 5. 2014, 3 pgs.

U.S. Appl. No. 13/725,030, Examiner Interview Summary mailed Jan. 22, 2015, 4 pgs.

U.S. Appl. No. 13/725,030, Examiner Interview Summary mailed Mar. 6, 2015, 3 pgs.

U.S. Appl. No. 13/725,030, Examiner Interview Summary mailed Jun. 29, 2015, 3 pgs.

U.S. Appl. No. 13/725,030, Final Office Action mailed May 19, 2015, 23 pgs.

U.S. Appl. No. 13/725,030, Non Final Office Action mailed Dec. 5, 2014, 19 pgs.

U.S. Appl. No. 13/725,030, Response filed Mar. 4, 2015 to Non Final Office Action mailed Dec. 5, 2014, 14 pgs.

U.S. Appl. No. 13/725,030, Response filed May 19, 2014 to Final Office Action mailed Mar. 17, 2014, 11 pgs.

U.S. Appl. No. 13/725,030, Response filed Aug. 25, 2015 to Final Office Action mailed May 19, 2015, 21 pgs.

U.S. Appl. No. 13/820,079, Advisory Action mailed Aug. 13, 2015, 3 pgs.

U.S. Appl. No. 13/820,079, Final Office Action mailed Apr. 23, 2015, 15 pgs.

U.S. Appl. No. 13/820,079, Non Final Office Action mailed Oct. 23, 2014, 14 pgs.

U.S. Appl. No. 13/820,079, Response filed Jan. 22, 2015 to Non Final Office Action mailed Oct. 23, 2014, 10 pgs.

U.S. Appl. No. 13/820,079, Response filed Jul. 23, 2015 to Final Office Action mailed Apr. 23, 2015, 10 pgs.

U.S. Appl. No. 13/913,974, Non Final Office Action mailed Aug. 24, 2015, 12 pgs.

U.S. Appl. No. 13/913,974, Response filed Aug. 10, 2015 to Restriction Requirement mailed Jun. 11, 2015, 7 pgs.

U.S. Appl. No. 13/913,974, Restriction Requirement mailed Jun. 11, 2015, 8 pgs.

Australian Application Serial No. 2010236855, First Amendment filed Aug. 6, 2014 to First Examiner Report mailed Jan. 17, 2014, 10 pgs.

Australian Application Serial No. 2013224686, First Examiner Report mailed Dec. 18, 2014, 2 pgs.

Australian Application Serial No. 2013224686, Voluntary Amendment filed Jun. 13, 2014, 15 pgs.

Austrialian Application Serial No. 2011295779, Examination Report mailed Jan. 30, 2015, 3 pgs.

Austrialian Application Serial No. 2011295779, Response filed Aug. 3, 2015 to Examination Report mailed Jan. 30, 2015, 14 pgs.

Canadian Application Serial No. 2,618,731, Office Action mailed Jun. 13, 2014, 2 pgs.

Canadian Application Serial No. 2,618,731, Response filed Dec. 12, 2014 to Office Action mailed Jun. 13, 2014, 28 pgs.

Chinese Application Serial No. 201180052952.2, Office Action mailed Apr. 17, 2014, (w/ English Translation), 21 pgs.

Chinese Application Serial No. 201180052952.2, Office Action mailed May 15, 2015 , (w/ English Translation), 31 pgs.

Chinese Application Serial No. 201180052952.2, Office Action mailed Dec. 18, 2014, (w/ English Translation), 11 pgs.

Chinese Application Serial No. 201180052952.2, Response filed Feb. 27, 2015 tp Office Action mailed Dec. 18, 2014, (w/ English Translation of Claims), 13 pgs.

Chinese Application Serial No. 201180052952.2, Response filed Jul. 30, 2015 to Office Action mailed May 15, 2015, (w/ English Translation of Amended Claims).

Chinese Application Serial No. 201180052952.2, Response filed Sep. 2, 2014 to Office Action mailed Apr. 17, 2014, (w/ English Translation of Claims), 14 pgs.

Chinese Application Serial No. 201210287455.7, Response filed Mar. 31, 2014 to Office Action mailed Nov. 14, 2013 , (w/ English Translation of Amended Claims), 9 pgs.

European Application Serial No. 10723848.7, Office Action mailed Jul. 8, 2014, 8 pgs.

European Application Serial No. 11181797.9, Office Action mailed Jul. 16, 2012, 2 pgs.

European Application Serial No. 11181797.9, Response filed Aug. 13, 2014 to Office Action mailed Feb. 3, 2014, 13 pgs.

European Application Serial No. 11181797.9, Result of Consultation mailed Jun. 26, 2014, 3 pgs.

European Application Serial No. 11776927.3, Response filed Jul. 2, 2015 to Telephone Interview on Jun. 23, 2015, 24 pgs.

(56) References Cited

OTHER PUBLICATIONS

European Application Serial No. 11776927.3, Response filed Aug. 15, 2015 to Examination Notification Art. 94(3) mailed Feb. 5, 2014, 9 pgs.

European Application Serial No. 11776927.3, Response filed Aug. 15, 2015 to Examination Notification Art. 94(3) mailed Feb. 5, 2014, 8 pgs.

European Application Serial No. 11776927.3, Result of Consultation mailed Jun. 29, 2015, 3 pgs.

European Application Serial No. 13732752.4, Office Action mailed Feb. 12, 2015, 2 pgs.

European Application Serial No. 13732752.4, Response filed Aug. 24, 2015 to Office Action mailed Feb. 12, 2015, 12 pgs.

Indian Application Serial No. 1741/DELNP/2008, Response filed May 28, 2014 to Office Action mailed Jun. 24, 2013, 13 pgs.

Israel Application Serial No. 215463, Office Action mailed Oct. 20, 2014, (English Translation), 3 pgs.

Israel Application Serial No. 233821, Office Action mailed Jul. 7, 2015, (English Translation), 2 pgs.

Japanese Application Serial No. 2012-248398, Amendment and Argument filed Aug. 18, 2014, (w/ English Translation), 50 pgs.

Japanese Application Serial No. 2012-248398, Examiners Decision of Final Refusal mailed Jan. 7, 2015, (w/ English Translation), 6 pgs.

Japanese Applicatin Serial No. 2012-503673, Argument and Amendment filed Nov. 28, 2014 in response to Office Action mailed Aug. 28, 2014, (w/ English Translation), 20 pgs.

Japanese Application Serial No. 2012-503673, Decision of Rejection mailed Apr. 22, 2015, (w/ English Translation), 6 pgs.

Japanese Application Serial No. 2012-503673, Office Action mailed Aug. 28, 2014, (w/ EnglishTranslation), 11 pgs.

Japanese Application Serial No. 2013-527329, Office Action mailed Jul. 8, 2015, (w/ English Translation), 12 pgs.

Japanese Application Serial No. 2015-94591, Amendment filed Jun. 5, 2015, (w/ English Translation), 5 pgs.

Korean Application Serial No. 10-2013-7028378, Response filed Mar. 24, 2014 to Notice of Preliminary Rejection mailed Jan. 24, 2014, (w/ English Translation of the Claims), 28 pgs.

Korean Application Serial No. 10-2014-7007674, Notice of Preliminary Rejection mailed Jun. 23, 2014, (w/ English Translation), 4 pgs.

"Lone bone", [online]. Wikipedia, the free encyclopedia. {retrieved on Aug. 18, 2015]. Retrieved from the Internet: <URL: http://en.wikipedia.org/wiki/Long-bone>, 2 pgs.

Russian Application Serial No. 2011143730, Office Action mailed Apr. 1, 2014, (w/ English Translation), 9 pgs.

Russian Application Serial No. 2011143730, Office Action mailed Sep. 19, 2014, (w/ English Translation), 7 pgs.

Russian Application Serial No. 2011143730, Response filed Aug. 28, 2014 to Office Action mailed Apr. 1, 2014, (w/ English Translation of Claims), 6 pgs.

Alberts, B., et al., "In: Molecular Biology of the Cell", (3rd Edition), Garland Publishing, New York and London, (1994), 971-977.

Barakat, O., et al., "Use of Decellularized Porcine Liver for Engineering Humanized Liver Organ", Journal of Surgical Research, 173(1), (2012), e11-e25.

Bauer, A., et al., "hDAF porcine cardiac xenograft maintains cardiac output after orthotopic gtransplantation into a baboon—a perioperative study", (Abstract), Xenotransplantation, 12(6), 444-449, (2005), 1 pg.

Bonandrini, Barbara, et al., "Recellularization of Well-Preserved Acellular Kidney Scaffold Using Embryonic Stem Cells", Tissue Engineering: Part A, vol. 20, Nos. 9 and 10, (2014), 1486-1498.

Czyz, Jaroslaw, et al., "Embryonic stem cell differentiation: The role of extracellular factors", Differentiation, 68, (2001), 167-174.

Downing, Gregory J., et al., "Technical Assessment of the First 20 Years of Research Using Mouse Embryonic Stem Cell Lines", Stem Cells, 22, (2004), 1168-1180.

Gilpin, Sarah E., et al., "Enhanced Lung Epithelial Specification of Human Induced Pluripotent Stem Cells on Decellularized Lung Matrix", Ann Thorac Surg, 98, (2014), 721-729.

Goh, S. K., et al., "Perfusion-decellularized pancreas as a natural 3D scaffold for pancreatic tissue and whole organ engineering.", Biomaterials, 34(28), (2013), 6760-6772.

Kang, Yu-Zhan, et al., "Decellularization technology application in which live reconstruct biological scaffold", National Medical Journal of China, vol. 89, No. 16, 1135-1138, (2009), 2 pgs.

Keller, Gorder, "Embryonic stem cell differentiation: emergence of a new era in biology and medicine", Genes & Development, 19, (2005), 1129-1155.

Liu, Xiaoqing, et al., "Elastic fiber homeostasis requires lysyl oxidase-like 1 protein", Nature Genetics, 36(2), (2004), 178-182.

Lu, Tung-Ying, et al., "Repopulation of decellularized mouse heart with human induced pluripotent stem cell-derived cardiovascular progenitor cells", Nature Communications, 4, (2013), 1-11.

Munoz-Elias, Guillermo, et al., "Marrow Stromal Cells, Mitosis, and Neuronal Differentiation: Stem Cell and Precursor Functions", Stem Cells, 21(4), (Jul. 2003), 437-448.

Oswald, Joachim, et al., "Mesenchymal Stem Cells can be Differentiated Into Endothelial Cells in Vitro", Stem Cells, 22(3), (2004), 377-384.

Robertson, Matthew J., et al., "Optimizing Recellularization of Whole Decellularized Heart Extracellular Matrix", PLoS One, 9(2): e90406, (Feb. 2014), 1-10.

Ross, Edward A, et al., "Embryonic Stem Cells Proliferate and Differentiate when Seeded into Kidney Scaffolds", Journal of the American Society of Nephrology, vol. 20, No. 11, (2009), 2338-2347.

Ross, Edward A., et al., "Mouse stem cells seeded into decellularized rat kidney scaffolds endothelialize and remodel basement membranes", Organogenesis, 8:2, (2012), 49-55.

Seaberg, R. M., et al., "Stem and progenitor cells: the premature desertion of rigorous definitions", Trends in Neurosciences, 26(3), (Mar. 2003), 125-131.

Song, J. J., et al., "Enhanced in Vivo Function of Bioartificial Lungs in Rats", Ann. Thorac. Surg., 92(3), (2011), 998-1006.

Song, Jeremy J., et al., "Regeneration and experimental orthotopic transplantation of a bioengineered kidney", Nature Medicine Advance Online Publication, Received Sep. 4, 2012; accepted Feb. 11, 2013; published online Apr. 14, 2013, (2013), 1-8.

Soto-Gutierrez, A., et al., "A Whole-Organ Regenerative Medicine Approach for Liver Replacement", Tissue Engineering Part C: Methods, 17(6), (2011), 677-686.

Suresh, Vijayan, et al., "A retrospective study of the prognostic impact of cytokine secretion in mixed lymphocyte culture on long-term graft function following allogeneic renal transplantation", Transpl Int., 18(9), (2005), 1067-1071.

Swanson, Julia C., et al., "Characterization of Mitral Valve Anterior Leaflet Perfusion Patterns", NIH Public Access, published in final edited form as: J. Heart Valve Dis., 18(5), (2009), 488-495.

(56) References Cited

OTHER PUBLICATIONS

Wang, Yunfang, et al., "Lineage Restriction of Human Hepatic Stem Cells to Mature Fates Is Made Efficient by Tissue-Specific Biomatrix Scaffolds", Hepatology, 53, (2011), 293-305.

Yagi, H., et al., "Human-Scale Whole-Organ Bioengineering for Liver Transplantation: A Regenerative Medicine Approach", Cell. Transplant., 22(2), (2013), 231-242.

Yang, Lijun, et al., "In vitro trans-differentiation of adult hepatic stem cells into pancreatic endocrine hormone-producing cells", Proc. Natl. Acad. Sci. USA, 99(12), (2002), 8078-8083.

Yasui, Haruyo, et al., "Excitation propagation in three-dimensional engineered hearts using decellularized matrix", Biomaterials, 35, (2014), 7839-7850.

\* cited by examiner

METHODS OF DECELLULARIZING BONE

CROSS-REFERENCE TO RELATED APPLICATIONS

The present application claims the benefit of the filing date of U.S. application Ser. No. 61/659,046, filed on Jun. 13, 2012, the disclosure of which is incorporated by reference herein.

BACKGROUND

Biologic scaffolds composed of extracellular matrix (ECM) which represents the secreted products of resident cells of each tissue and organ, are increasingly used in regenerative medicine strategies for tissue and organ replacement. Preservation of the native ultrastructure and composition of ECM during the process of tissue decellularization is highly desirable (Ott et al., Nat. Med., 14:213 (2008); Uygun et al., Nat. Med., 16:814 (2010); Petersen et al., Science, 329:538 (2010); Nakayama et al., Tissue Eng. Part A, 16:2207 (2010); Allen et al., Tissue Eng. Part A, 16:3363 (2010); Simionescu et al., J. Heart Valve Dis., 12:226 (2003); Badylak et al., Acta Biomater., 5:1 (2009)). Numerous methods have been employed to decellularize tissues and organs and those methods may result in decellularized tissues and organs with different mechanical and biological properties. For example, certain chemicals and solutions, e.g., acids, bases, hypotonic solution, hypertonic solution, detergents, alcohols, chelating agents, and other solvents, enzymes such as nucleases, collegenases and lipases, and physical treatments including temperature, force and pressure, non-thermal electroporation, have been employed to decellularize tissues and organs.

Autograft bone long has been the preferred implant for most bone graft procedures in the United States. Autograft bone is a desirable graft source because it provides a scaffold for osteoconduction, contains noncollagenous bone matrix proteins that stimulate osteoinduction, and incorporates progenitor stem cells for osteogenesis.

Despite its wide prevalence, the use of autograft material poses several disadvantages. At best, the need to harvest the autograft from the iliac crest, proximal tibia or distal femur presents the obvious drawbacks of the discomfort, time and expense of two procedures to accommodate the patient's need for bone grafting. At worst, the initial harvesting procedure can precipitate chronic pain, significant blood loss, infection and other iatrogenic complications, prolonged hospital stay and recovery time. The second surgery also adds substantially to the cost of the overall bone graft process. Additionally, the autograft material is collected in fragments, which is sufficient as a bone filler for small voids, but offers minimal structural stability.

While cadaver-derived allograft, the second most frequent material, precludes the need for a second surgery and can be used for large, load bearing applications, the grafted bone may be incompatible with, and ultimately rejected by, the host bone due to the cellular material still present. In addition, the effectiveness of allograft material is inconsistent. The processing of allograft tissue to lower contamination risk also can substantially degrade the biologic and mechanical properties initially present in the donated tissue.

The inherent shortcomings of both autografts and allografts have driven the development of synthetic bone graft substitutes, however, synthetic materials are currently used in only ten percent of orthopedic procedures worldwide. Biosynthetic and synthetic materials now available to orthopedic and spinal surgeons include demineralized bone matrix, collagen, ceramics, cements, and polymers, such as silicone and some acrylics. These materials can serve as a structure on which new bone can grow. Many of these materials then dissolve over time, leaving new bone behind. The benefits of these synthetic grafts include availability, sterility and reduced morbidity. However, many of them lack the osteoinductive properties of native bone.

SUMMARY OF THE INVENTION

The invention provides a method to decellularize a mammalian bone or a portion thereof. In one embodiment, the invention provides a method of decellularizing a native mammalian bone, for example, a bone having cortical (compact) bone, cancellous (spongy) bone, a central (medullary) cavity, and cells, that is isolated from a mammal. In order to decellularize that native bone, one or more apertures (one or more openings) are introduced from the exterior of the bone into the central cavity. The one or more apertures are individually fitted, or a plurality of the apertures are fitted, with an apparatus that provides a water tight seal and one or more (non-native) conduits for fluid passage. A cellular disruption medium is perfused into the central cavity of the bone via the apparatus under conditions that provide for decellularization of the bone. For example, a long bone may be cannulated through an aperture of about ⅛ inch in diameter up to the diameter of the medullary canal of the bone. If the bone does not contain a medullary canal, the largest diameter would be determined by the size of the fitting that could appropriately seal the face of the bone, which aperture optionally may be further modified to provide for a water tight seal with the apparatus, e.g., by introducing at least two to three threads, and a cellular disruption medium perfused into the central cavity under conditions that provide for decellularization. In one embodiment, the medium having cells and/or cellular debris flows out of the native arterial and/or venous structures in the bone. The decellularized bone has the mechanical and biochemical properties of native bone and includes the extracellular matrix of the native vascular structures.

In one embodiment, the invention provides a method of decellularizing a native mammalian bone, for example, a bone having cortical bone, cancellous bone, a central cavity, and cells, that is isolated from a mammal. In order to decellularize that native bone, the end of the bone is pressurized which drives cells and cellular debris out through one of the natural conduits at the other end of the bone. In another embodiment, the end of the bone is pressurized and an exit path is introduced at the other end of the bone, e.g., by cutting or drilling into the bone to provide aperture.

In one embodiment, the method provides for decellularizing a portion of a mammalian bone having cortical bone, cancellous bone, a central cavity, and cells. The method includes providing a transverse portion of a mammalian bone having cortical bone, cancellous bone, a central cavity, and cells. The portion is fitted with an apparatus that provides a water tight seal and one or more conduits for fluid passage. A cellular disruption medium is perfused into the central cavity of the bone via the apparatus under conditions that provide for decellularization of the portion of the bone. In one embodiment, before being fitted with the apparatus, the central cavity is modified, e.g., via drilling, to adapt to fit the conduit. In one embodiment, the central cavity is modified to include threads to match threads in the conduit in the apparatus. In one embodiment, the apparatus has one conduit adapted to fit the central cavity and after the apparatus is sealed to the portion of the bone, cellular disruption medium is introduced to the cavity and the effluent which contains cells and/or cellular debris exits from the arterial and/or venous structures, osteons, lamellae, Haversian canals and/or Volkmann's canals. The decellularized portion of bone has the mechanical and biochemical properties of native bone and includes the extracellular matrix of the native vascular structures.

For example, a native bone is cut (severed) near the femoral head or near the condyles, providing a portion of a bone that is transversely cut (a cross-section with one end having a native configuration). In one embodiment, a native bone is cut (severed) near the femoral head and near the condyles, providing a portion of a bone that is transversely cut (a cross-section with both ends having an exposed central cavity). In one embodiment, material in the central cavity, e.g., marrow, near the exogenously introduced opening is removed to allow for better perfusion. In one embodiment, the central cavity is modified by drilling and tapping, or just tapping, the diaphysis, e.g., to create threads. The apparatus that is attached to the transverse end of the portion of the bone has at least one sleeve (an exterior sleeve) and a least one conduit to introduce fluid into at least the central cavity, which apparatus provides for a water tight seal. In one embodiment, the exterior sleeve is tapered. A seal may be created between the exposed end of the portion of the bone by any means. For instance, a clamp, e.g., a tube clamp, worm gear clamp or quick clamp, or a cable tie, may be employed to create a seal between the exterior sleeve and the circumference of the portion of the bone. In one embodiment, the apparatus includes a fitting that is adapted to thread into threads introduced to the central cavity. In one embodiment, the apparatus includes a fitting that is adapted to thread into threads introduced on the circumference of the portion of the bone. In one embodiment, the conduit may be tubing. In one embodiment, the apparatus has an exterior sleeve and an interior barrier so that fluid under different flow conditions may introduced to the central cavity and to the compact bone. The flow conditions may also include negative pressure to pull solution in through the native vasculature when placed in a solution.

In one embodiment, a threaded fitting is employed, e.g., NPT, Straight, Tapered, BSPP, etc.) and that fitting may be sealed in a variety of ways including but not limited to teflon tape, o-ring, silicone grease, or superglue/adhesive. In one embodiment, an aperture of about ⅛ inch to about ¾ inch is introduced into a native bone to provide access to the central cavity. In one embodiment, the aperture has at least two to three threads and an apparatus that has a fitting that has complementary threads is fitted to the aperture. In one embodiment, a transverse portion of a bone is modified to include at least two to three threads and an apparatus having a sleeve and a fitting that has complementary threads is fitted to the exposed (transverse) portion of the bone. In one embodiment, a NPTF fitting is employed, e.g., one that does require additional components (Teflon tape, o-rings, silicone grease, or super glue/adhesive, etc.) to create a water tight seal.

In one embodiment, an aperture in the bone is created and a cannula is press fit into the aperture to form a water tight seal. That cannula may also have a flange attached to it that can be fixed to the bone using a variety of clamping mechanisms (cable ties, worm gear clamps, quick release clamps, or any other clamps) to the bone in order to form a water tight seal. The flange could also include holes which would allow the plate to be fixed to the bone using screws. These could be self tapping screws or bolts that thread into the bone face.

In one embodiment, the apparatus may include stainless steel tubing. In one embodiment, a fluid circuit is connected to a piston which is coupled to a pneumatic, hydraulic, or electric actuator, thereby allowing for significantly higher pressures to be delivered to the interior of the bone. In this embodiment, to facilitate continuous long term pressurization, a secondary reservoir of fluid may be connected to the piston via a high pressure valve. This valve would open each time the piston finished a stroke so as to draw more fluid into the piston cavity when pulling the piston back to its home position and thus reloading it for cyclic pressurization.

In one embodiment, the apparatus may include flexible tubing. In one embodiment, a fluid circuit is connected to a pump apparatus (including but not limited to: peristaltic, piston, gear, centrifugal, diaphragm, or positive displacement pumping mechanisms).

In one embodiment, the decellularization methods employ a cellular disruption medium which includes a detergent. In one embodiment, the detergent is an anionic detergent. In one embodiment, the bone is a human bone. In one embodiment, the bone is a long bone. In one embodiment, a portion of a bone, e.g., a portion that includes a diaphysis, is decellularized.

The decellularized bone or portion hereof prepared as described herein provides for a bone graft product with autograft properties as a result of the removal of the cellular material from the bone while leaving all the appropriate matrix factors and cytokines that enable the graft to be both osteoconductive and osteoinductive. Additionally, the majority of the bone structure is left intact to provide significant structural and functional support in load bearing applications and includes the native vascular bed for enhanced revascularization.

In one embodiment, a decellularized bone or portion thereof is recellularized with cells, e.g., vascular progenitor cells or primary vascular cells, under conditions such as perfusion in biocompatible media at physiological pressures for a period of time, e.g., about 1 to about 14 days.

DETAILED DISCLOSURE

Figure 1:
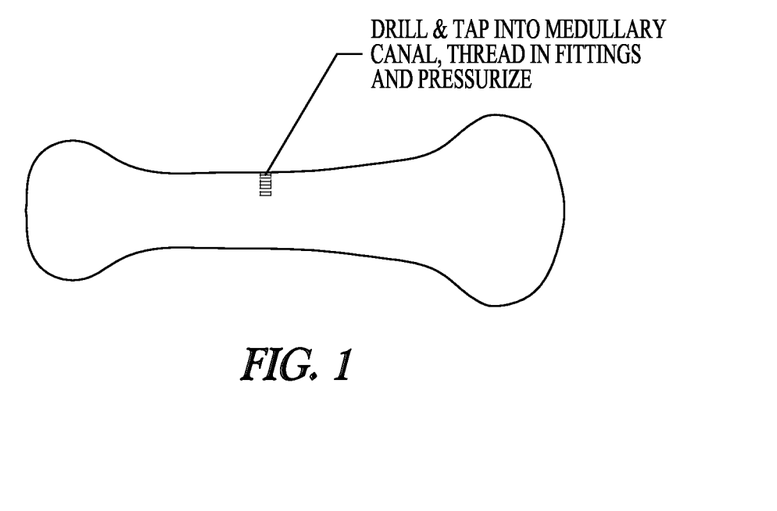
FIG. 1. Exemplary embodiment of a bone that has an aperture that has been drilled and tapped to allow for access to the central cavity, which aperture can include threads which are compatible with threads in an apparatus that is employed to perfuse fluids into the bone.
Figure 2:
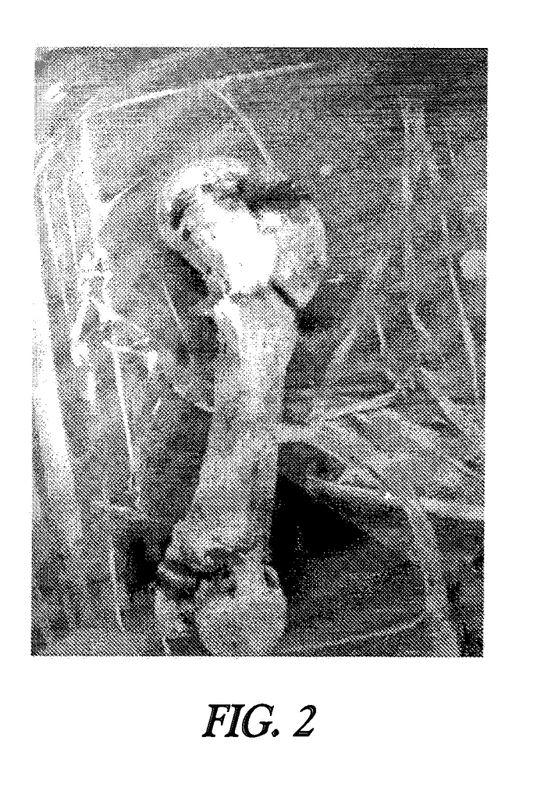
FIG. 2. Photograph of a cannulated long bone accessed through a ¼ inch hole. Perfusion of 0.5% SDS using a pressure of about 200 to about 1000 mm Hg provided for decellularization of the bone with the effluent exiting through the native arterial and venous structures.
Figure 3:
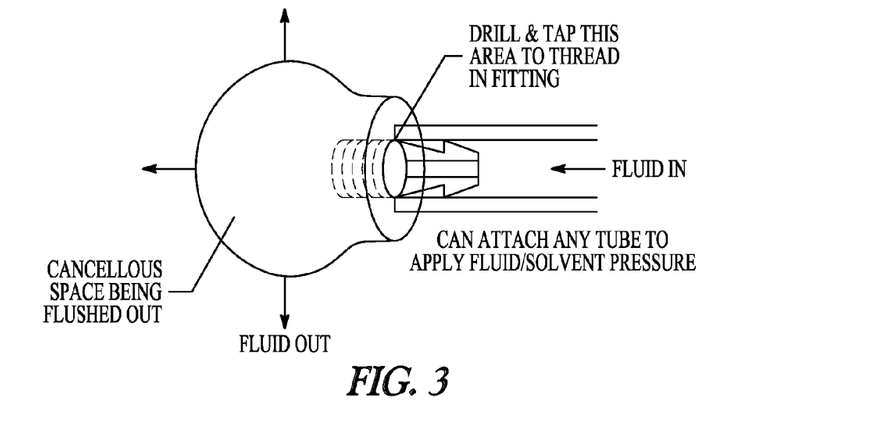
FIG. 3. Exemplary embodiment of a bone fitted with an apparatus adapted to introduce fluid to the central cavity of the bone. In this embodiment, the central cavity is tapped to create threads into which a fitting in the apparatus is screwed. The direction of fluid flow is shown.
Figure 4:
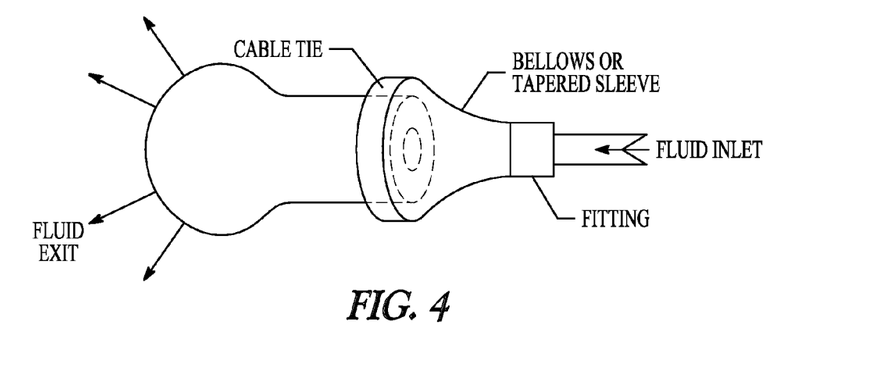
FIG. 4. Exemplary embodiment of a portion of a bone fitted with an apparatus having a sleeve, e.g., a bellows or fitted sleeve, which is attached to the exterior of the bone via a clamp. The direction of fluid flow is shown.
Figure 5:
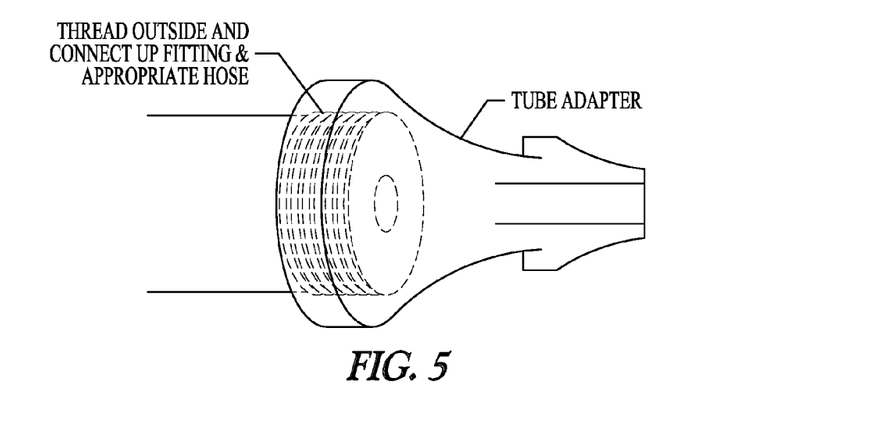
FIG. 5. Exemplary embodiment of a portion of a bone fitted with an apparatus adapted to introduce fluid to the central cavity of the bone. In this embodiment, the exterior surface of the bone is drilled and tapped to create threads into which a fitting in the apparatus is screwed.
Figure 6:
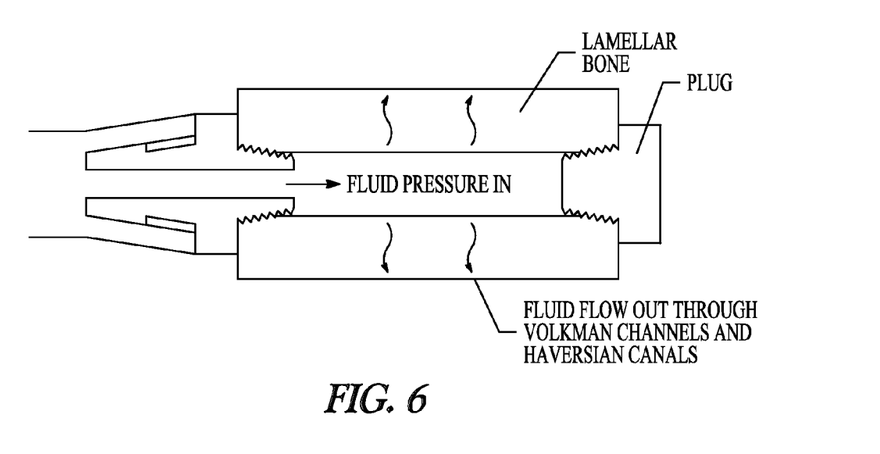
FIG. 6. Exemplary embodiment of a portion of a bone that has an exogenously introduced aperture at each end, that is fitted at one end with an apparatus adapted to introduce fluid to the central cavity of the bone, and fitted at the other end by a plug. The direction of fluid flow is shown.
Figure 7:
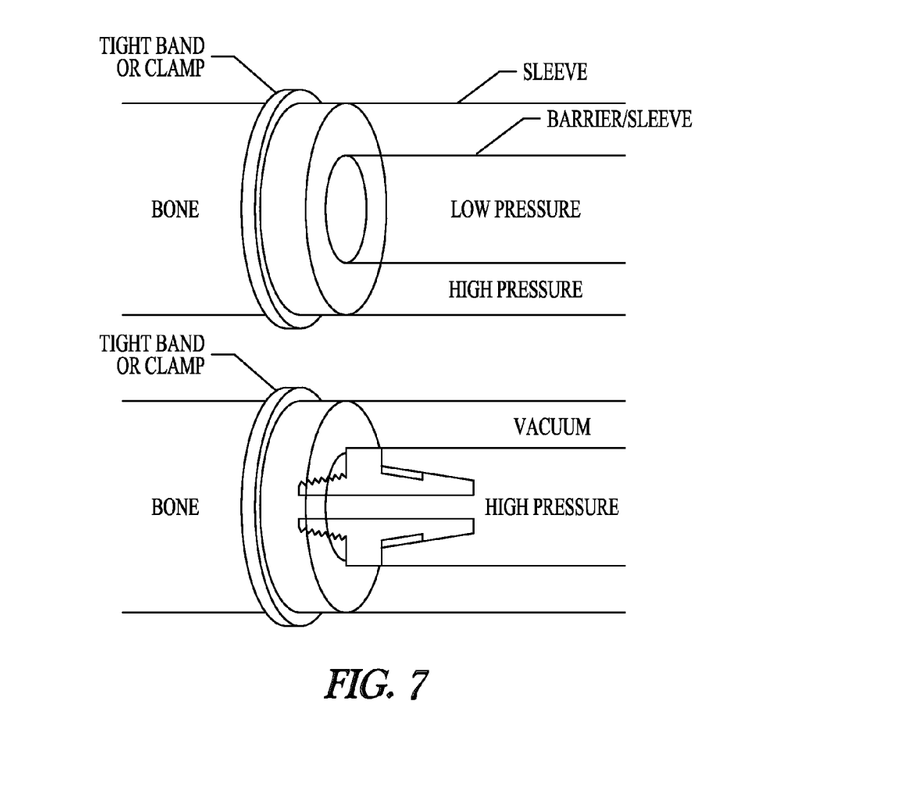
FIG. 7. A) An apparatus having two sleeves that provide two separate conduits is adapted to perfuse fluid under low pressure to the central cavity and perfuse fluid under high pressure to the compact bone. B) An apparatus having two conduits, one of which allows for perfusion of fluid under high pressure to the central cavity and the other of which allows for a significantly lower pressure or negative pressure to draw fluid and cells out of the compact bone. In an alternative embodiment, an apparatus has the same two conduits, one of which allows for perfusion at a high pressure to the compact bone and a significantly lower or negative pressure in the central cavity to draw fluid and cells out through the central cavity.

Perfusion decellularization is an ex vivo method of decellularizing a mammalian organ, part (portion) of an organ or vascularized tissue where a decellularization solution is perfused through organ, part of an organ or vascularized tissue to facilitate decellularization while maintaining the vascular conduits. The resulting decellularized organ, matrix, tissue scaffold or graft retains a vascular system comprising of an arterial supply, interstial space where capillary beds reside and venous output such that fluid or cells can be introduced via one or more entry points, and exit the organ, matrix, tissue or graft through a different route.

The invention provides for active access to the marrow cavity or inner vascular networks via a sealed access followed by perfusion, e.g., high pressure perfusion, of a cellular disruption medium for the removal of cellular material from the bone. For example, after introducing an aperture into the bone, an apparatus having a fitting is attached to the aperture. In one embodiment, a peristaltic pump is used to pump cellular disruption medium into the central cavity or cancellous bone compartment. The cellular disruption medium permeates throughout the bone, including the periostium, via various arterial and venous vessels, as well as other native conduits, eventually exiting the bone via the arterial and venous vasculature or other conduits. Alternatively, a peristaltic pump is used to create negative pressure in the central cavity or cancellous bone compartment. The bone or bone fragment is placed into cellular disruption medium and the medium permeates through the periosteum and into the bone through the arterial and venous vessels and permeates throughout the bone exiting through the central cavity or cancellous bone compartment via the pump. Alternatively, a long bone can be circumferentially cut exposing the central cavity of the bone. The marrow may be washed out using direct flow and then the cut end of the bone may be sealed with an apparatus having an outside fitting capable of being attached to tubing, creating a tight water seal to the bone. Cellular disruption medium is then pumped into the bone at high pressures to provide access to the entire bone via the arterial and/or venous structures, and/or other structures. The cellular disruption medium exits the bone through, for example, native arterial and venous structures, providing a continuous flow through circuit. Any bone may be cannulated and perfused with the intent to decellularize the bone structure.

Decellularization of a bone or a portion thereof as described herein thus removes most or all of the cellular components while substantially preserving the extracellular matrix (ECM) and other structures, e.g., vascular structures, the Haversian canals, Volkmann's canals, lacunae, lamellae, canaliculi, osteon, periosteum, trabecluae, and combinations thereof. A decellularized bone or a portion thereof then can be used as a scaffold for recellularization, e.g., ex vivo or in vivo. Mammals from which bones can be obtained include, without limitation, rodents, pigs, rabbits, cattle, sheep, dogs, and humans. Bones used in the methods described herein may be cadaveric.

Post decellularization, the bone can be isolated for use in various orthopedic applications including the use of whole bone, portions of the bone, or morsalized pieces. Since the bone retains its native ECM and mechanical properties, the bone can also be recellularized or seeded with cells including, bone marrow aspirate, mononuclear cells, endothelial cells, stem cells, bone specific cells, and the like. This recellularized tissue offers advantages over autograft tissue because it is able to provide functional mechanical support to a large injury, void, or resection site. A decellularized bone or any portion thereof, with or without recellularization, can be used for transplanting into a patient Exemplary Bones for Use in the Methods of the Invention Long bones, short bones, flat bones and other bones may be employed in the methods of the invention so long as the bone has dimensions that allow for connecting an apparatus, e.g., one having a fitting, which facilitates perfusion of a fluid through the bone or portion thereof at a set pressure or via a pressure gradient that forces the decellularization solution through the bone. A native bone or portion thereof with one or more exogenously introduced apertures fitted with one or more apparati may be considered a "closed" system which holds pressure during perfusion through it, e.g., the aperture(s) is/are sealed such that a defined pressure may be maintained at a flow rate >0 mL/minute. For instance, a bone or a portion thereof for decellularization may be at least about 12 $cm^3$ or greater in size.

Long bones are characterized by a shaft, the diaphysis, that is much longer than it is wide. They are made up mostly of compact bone, with lesser amounts of marrow, located within the medullary cavity, and spongy bone. The outer surface of the bone also may contain periostium. Most bones of the limbs, including those of the fingers and toes, are long bones. The exceptions are those of the wrist, ankle and kneecap. Short bones are roughly cube-shaped, and have only a thin layer of compact bone surrounding a spongy interior. The bones of the wrist and ankle are short bones, as are the sesamoid bones. Flat bones are thin and generally curved, with two parallel layers of compact bones sandwiching a layer of spongy bone. Most of the bones of the skull are flat bones, as is the sternum.

Compact (cortical) bone is the hard outer layer of bones that is composed of parallel cylindrical units packed tightly together called osteons, and has a porosity of about 5% to about 30%. Within the osteons are concentric tubes of bone called lamella. The interfaces between the lamellae are lined with voids termed lacunae, which house bone cells that respond to mechanical signals. These units are aligned in an anisotropic fashion to maximize the mechanical properties of the material. Trabecular (cancellous or spongy) bone fills the ends of long bones, and is composed of a network of rod- and plate-like elements that make the overall organ lighter and allow room for blood vessels and marrow. While it is also anisotropic in response to mechanical loading, on average, it possesses an apparent stiffness and elastic modulus one order of magnitude lower than its more dense counterpart. Trabecular bone accounts for the remaining 20% of total bone mass but has nearly ten times the surface area of compact bone, and its porosity ranges from 30% to 90%. Mineralized matrix surrounds blood vessels in the canalicular network in compact bone, while marrow and blood surround bone in cancellous bone.

Bones include four major types of cells that are removed by the decellularization methods of the invention including osteoblasts, osteocytes, bone-lining cells and osteoclasts. Osteoblasts are mononucleate bone-forming cells that descend from osteoprogenitor cells. They are located on the surface of osteoid seams and make a protein mixture known as osteoid, which mineralizes to become bone. Osteoid is primarily composed of Type I collagen. Osteoblasts also manufacture hormones, such as prostaglandins, to act on the bone itself, alkaline phosphatase, an enzyme that has a role in the mineralisation of bone, as well as many matrix proteins. Osteoblasts are the immature bone cells, and eventually become entrapped in the bone matrix to become osteocytes—the mature bone cell. Osteocytes originate from osteoblasts that have migrated into and become trapped and surrounded by bone matrix that they themselves produce. The spaces they occupy are known as lacunae. These cells primarily sense mechanical load or tissue damage and subsequently can initiate remodeling responses. It has been postulated that osteocytes initiate remodeling by detecting strains in the bone matix or by responding to flow mediated shear stresses in the fluid filled lacunae due to bone deformation during loading. Osteocyte functions include, formation of bone; matrix maintenance and calcium homeostasis. Bone-lining cells, which cover resting bone surfaces, also share mechanosensation and adaptation duties. Lining cells can differentiate into an "osteoblastic" state as well as recruit osteoprogenitor cells. Additionally, lining cells are also instrumental in bone resorption by (1) recruiting osteoclasts (bone resorption cells) to resorption sites, (2) boosting the differentiation of osteoclast precursors, and (3) preparing the bone surface for resorption. Osteoclasts are the cells responsible for bone resorption, thus they break down bone. New bone is then formed by the osteoblasts (remodeling of bone to reduce its volume). Osteoclasts are large, multinucleated cells located on bone surfaces in what are called Howship's lacunae or resorption pits. These lacunae, or resorption pits, are left behind after the breakdown of the bone surface.

The majority of bone is made of the bone matrix. It has inorganic and organic parts. The inorganic composition of bone (bone mineral) is formed from carbonated hydroxyapatite ($Ca_{10}(PO_4)_6(OH)_2$) with lower crystallinity. The organic part of matrix is mainly composed of Type I collagen. This is synthesised intracellularly as tropocollagen and then exported, forming fibrils. The organic part is also composed of various growth factors, the functions of which are not fully known. Factors present include glycosaminoglycans, osteocalcin, osteonectin, bone sialo protein, osteopontin and cell attachment factor. One of the characteristics that distinguishes the matrix of bone from that of another cell is that the matrix in bone is mineralized.

Lamellar bone, which has a regular parallel alignment of collagen into sheets (lamellae). Lamellar bone is filled with many collagen fibers parallel to other fibers in the same layer (these parallel columns are called osteons).

Decellularization of Bones or Portions Thereof

The invention provides for methods and materials to decellularize a mammalian bone or a portion thereof. The initial step in decellularizing a bone or a portion thereof is to introduce an aperture to or to otherwise access, e.g., by a transverse cutting of the bone which provides a cross-section, drilling, etc., the central cavity. The aperture may then be fitted with an apparatus that provides a water tight seal and a conduit for fluid (e.g., a cannula) so that an aqueous liquid can be introduced to at least the central cavity under pressure, positive or negative. Then the bone or portion thereof is perfused with a cellular disruption medium. Perfusion may be multi-directional, alternated, retrograde, antegrade, both or combination thereof, and may be conducted under different conditions for compact bone and cancellous bone. In one embodiment, a reservoir containing cellular disruption medium is attached via the apparatus such as one described herein to the bone or portion thereof. A cellular disruption medium may be delivered either at a constant or varying flow rate, for example, by an infusion or roller pump or by a constant or varying hydrostatic pressure. In both instances, the perfusion fluid is directed into at least the central cavity, which then drains into the Haversian canals, Volkmann's canals, lamellae, osteons, or any combination thereof, which provide for an egress. Alternatively, in another embodiment the cellular disruption medium may be delivered either at a constant or varying flow rate, for example, by an infusion or roller pump or by a constant or varying negative hydrostatic pressure. In both instances, the perfusion fluid is directed into the bone through atrial and venous vessels, through the Haversian canals, Volkmann's canals, lamellae, osteons, or any combination thereof, which provide for an egress into the central cavity.

One or more cellular disruption media can be used to decellularize. A cellular disruption medium useful in the methods of the invention include but is not limited to acidic solutions, basic solutions, hypotonic solutions, hypertonic solutions, or solution having detergents such as non-ionic detergents, e.g., Triton X-100, ionic detergents such as SDS, sodium deoxycholate, or Triton X-200, zwitterionic detergents, solvents such as alcohol, acetone, tributyl phosphate, nuclease, one or more DNases, proteases such as trypsin, one or more collagenases, one or more dispases, a chelating agent, or any combination thereof. A cellular disruption medium can include water such that the medium is osmotically incompatible with the cells. Alternatively, a cellular disruption medium can include a buffer (e.g., PBS) for osmotic compatibility with the cells. In some instances, cellular disruption media also or alternatively can include inhibitors of one or more enzymes (e.g., protease inhibitors, nuclease inhibitors, and/or collagenase inhibitors). In one embodiment, the cellular disruption medium comprises SDS, e.g., about 0.01% to about 5.0%.

In certain embodiments, a bone or portion thereof can be perfused sequentially with two different cellular disruption media. For example, the first cellular disruption medium can include an anionic detergent such as SDS and the second cellular disruption medium can include an ionic detergent such as Triton X-100. Following perfusion with at least one cellular disruption medium, a bone or portion thereof can be perfused, for example, with wash solutions and/or solutions containing one or more enzymes such as those disclosed herein.

Decellularization as described herein essentially decellularizes the bone from the inside out, resulting in very little damage to the ECM. A bone or portion thereof can be decellularized at a suitable temperature between 4 and 40° C. Depending upon the size and weight of a bone or portion thereof and the particular agent(s) in the cellular disruption medium and concentration of agent(s) in the cellular disruption medium, a bone or portion thereof generally is perfused from about 0.5 to about 80 hours with cellular disruption medium. Including washes, an organ may be perfused for up to about 1 to about 100 hours. Perfusion may be adjusted via pulsatile flow, direction, rate, and/or pressure. Perfusion may be conducted under pressures ranging from about 10 to about 2000 mm Hg. In one embodiment, a pressure gradient is employed with a cellular disruption medium to decellularize bone or a portion thereof. For example, a pressure of about 1000 mm Hg ("high" pressure) may be employed to introduce cellular disruption media into the canalicular network (e.g., Haversian and Volkmann's canals), while a lower pressure, for instance, about 300 mm Hg, may be used for the central cavity, which may increase the flow of fluid in the outer cortical bone compared to just pressurizing the central cavity. In another embodiment, high pressure is employed to introduce the cellular disruption medium into the central cavity and a vacuum is employed to draw the effluent through the cortical bone.

Decellularization may be monitored by measuring DNA content, cellular membranes, hemoglobin, protein, or substantial absence of nuclei (e.g., using histological methods) in effluent from the bone or portion thereof. In one embodiment, DNA levels in the effluent are less than about 100 ng/mg of bone. As indicated herein, a decellularized bone or portion thereof has the extracellular matrix (ECM) component of all or most regions of the bone or portion thereof, including ECM components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. Organized mineralized matrix is also a significant component of bone's ECM. Successful decellularization may be monitored by cell components such as double-stranded DNA (dsDNA), mitochondria, or membrane-associated molecules such as phospholipids are detected. For example, <100 ng dsDNA per mg ECM dry weight, <200 bp DNA fragment length and/or lack of visible nuclear material in tissue sections stained with 4',6-diamidino-2-phenylindole (DAPI) or H&E may be employed to determine that a particular bone or portion thereof subjected to decellularization methods is effectively (substantially) decellularized.

DNA is directly correlated to adverse host reactions, is ubiquitous across tissue and cell types, is readily assayed, and provides a general index for other cell residues within ECM. DNA and mitochondria are easily quantified using commercially available dsDNA intercalators such as PicoGreen, propidium iodide, or bisbenzimide and by gel electrophoresis, respectively. Routine histologic staining or immunofluorescent methods may also be employed. It should be noted that histologic stains such as H&E or trichrome provide relatively insensitive methods for identifying and qualitatively analyzing DNA within ECM. Residual phospholipids can be quantified using enzyme-based assays.

One or more compounds can be applied in or on a decellularized bone or portion thereof, for example, preserve, or to prepare it for recellularization and/or to assist or stimulate cells during the recellularization process. Such compounds include, but are not limited to, one or more growth factors (e.g., VEGF, DKK-1, FGF, BMP-1, BMP-2, BMP-4, SDF-1, IGF, and HGF), immune modulating agents (e.g., cytokines, glucocorticoids, IL2R antagonist, leucotriene antagonists), and/or factors that modify the coagulation cascade (e.g., aspirin, heparin-binding proteins, and heparin). In addition, a decellularized bone or portion thereof be further treated with, for example, irradiation (e.g., UV, gamma, e-beam) to reduce or eliminate the presence of any type of microorganism remaining on or in it.

Recellularization of Bones or Portions Thereof

To effectively recellularize, it is important that the morphology and the architecture of the ECM be maintained (i.e., remain substantially intact) during and following the process of decellularization. "Morphology" as used herein refers to the overall shape of the ECM, while "architecture" as used herein refers to the relationship between other bone components to the ECM. The morphology and architecture of the ECM can be examined visually and/or histologically.

The invention provides for materials and methods for generating at a minimum, functional mineralized matrix, up to complete bone or portion thereof. A bone or portion thereof can be generated by contacting a decellularized bone or portion thereof as described herein with a population of regenerative cells. Regenerative cells as used herein are any cells used to recellularize a decellularized organ or tissue. Regenerative cells can be totipotent cells, pluripotent cells, or multipotent cells, and can be uncommitted or committed. Regenerative cells also can be single-lineage cells. In addition, regenerative cells can be undifferentiated cells, partially differentiated cells, or fully differentiated cells. Regenerative cells as used herein include embryonic stem cells (as defined by the National Institute of Health (NIH); see, for example, the Glossary at stemcells.nih.gov on the World Wide Web). Regenerative cells also include progenitor cells, precursor cells, and "adult"-derived stem cells including umbilical cord cells and fetal stem cells.

Examples of regenerative cells that can be used to recellularize a bone or portion thereof include, without limitation, embryonic stem cells, umbilical cord blood cells, tissue-derived stem or progenitor cells, bone marrow-derived stem or progenitor cells, endothelial cells, blood-derived stem or progenitor cells, adipose tissue-derived stem or progenitor cells, mesenchymal stem cells (MSC), skeletal muscle-derived cells, amniotic fluid stem cells (AFSC), or multipotent adult progenitor cells (MAPC). Bone marrow-derived stem cells such as bone marrow mononuclear cells (BM-MNC), endothelial or vascular stem or progenitor cells, bone marrow aspirate, and peripheral blood-derived stem cells such as endothelial progenitor cells (EPC) also can be used as regenerative cells.

The number of regenerative cells that is introduced into and onto a decellularized bone or portion thereof in order to generate a bone or portion thereof is dependent on both the bone or portion thereof (e.g., which bone, the size, surface area, and weight of the bone) and the type and developmental stage of the regenerative cells. Different types of cells may have different tendencies as to the population density those cells will reach. Similarly, different bones or portions thereof may be recellularized at different densities. By way of example, a decellularized bone or portion thereof can be "seeded" with at least about 1,000 (e.g., at least 10,000, 100,000, 1,000,000, 10,000,000, or 100,000,000) regenerative cells; or can have from about 1,000 cells/mg tissue (i.e., prior to decellularization) to about 10,000,000 cells/mg tissue attached thereto. Regenerative cells can be introduced ("seeded") into a decellularized bone or portion thereof by injection into one or more locations. In addition, more than one type of cell (i.e., a cocktail of cells) can be introduced into a decellularized bone or portion thereof. For example, a cocktail of cells can be injected at multiple positions in a decellularized bone or portion thereof or different cell types can be injected into different portions of a decellularized bone or portion thereof. Alternatively, or in addition to injection, regenerative cells or a cocktail of cells can be introduced by perfusion into a decellularized bone or portion thereof. For example, regenerative cells can be perfused into a decellularized bone or portion thereof using a perfusion medium, which can then be changed to an expansion and/or differentiation medium to induce growth and/or differentiation of the regenerative cells.

During recellularization, a bone or portion thereof is maintained under conditions in which at least some of the regenerative cells can multiply and/or differentiate within and on the decellularized bone or portion thereof. Those conditions include, without limitation, the appropriate temperature and/or pressure, the appropriate amounts of $O_2$ and/or $CO_2$, an appropriate amount of humidity, and sterile or near-sterile conditions. During recellularization, the decellularized bone or portion thereof and the regenerative cells attached thereto are maintained in a suitable environment. For example, the regenerative cells may require a nutritional supplement (e.g., nutrients and/or a carbon source such as glucose), exogenous hormones or growth factors, a mineral source (e.g. β-Glycerophosphate), ascorbic acid and/or a particular pH.

Regenerative cells can be allogeneic to a decellularized bone or portion thereof (e.g., a human decellularized bone or portion thereof seeded with human regenerative cells), or regenerative cells can be xenogeneic to a decellularized bone or portion thereof (e.g., a pig decellularized bone or portion thereof seeded with human regenerative cells). "Allogeneic" as used herein refers to cells obtained from the same species as that from which the bone or portion thereof originated (e.g., self (i.e., autologous) or related or unrelated individuals), while "xenogeneic" as used herein refers to cells obtained from a species different than that from which the bone or portion thereof originated.

In some instances, a bone or portion thereof generated by the methods described herein is to be transplanted into a patient. In those cases, the regenerative cells used to recellularize a decellularized bone or portion thereof can be obtained from the patient such that the regenerative cells are "autologous" to the patient. Regenerative cells from a patient can be obtained from, for example, blood, bone marrow, tissues, or organs at different stages of life (e.g., prenatally, neonatally or perinatally, during adolescence, or as an adult) using methods known in the art. Alternatively, regenerative cells used to recellularize a decellularized bone or portion thereof can be syngeneic (i.e., from an identical twin) to the patient, regenerative cells can be human lymphocyte antigen (HLA)-matched cells from, for example, a relative of the patient or an HLA-matched individual unrelated to the patient, or regenerative cells can be allogeneic to the patient from, for example, a non-HLA-matched donor.

Irrespective of the source of the regenerative cells (e.g., autologous or not), the decellularized bone or portion thereof can be autologous, allogeneic or xenogeneic to a patient.

In certain instances, a decellularized bone or portion thereof may be recellularized with cells in vivo (e.g., after the organ or tissue has been transplanted into an individual). In vivo recellularization may be performed as described above (e.g., injection and/or perfusion) with, for example, any of the regenerative cells described herein. Alternatively or additionally, in vivo seeding of a decellularized bone or portion thereof with endogenous cells may occur naturally or be mediated by factors delivered to the recellularized bone or portion thereof.

The progress of regenerative cells can be monitored during recellularization. For example, the number of cells on or in a bone or portion thereof can be evaluated by taking a biopsy at one or more time points during recellularization. In addition, the amount of differentiation that regenerative cells have undergone can be monitored by determining whether or not various markers are present in a cell or a population of cells. Markers associated with different cells types and different stages of differentiation for those cell types are known in the art, and can be readily detected using antibodies and standard immunoassays. See, for example, *Current Protocols in Immunology,* 2005, Coligan et al, Eds., John Wiley & Sons, Chapters 3 and 11. Nucleic acid assays as well as morphological and/or histological evaluation can be used to monitor recellularization. Functional analysis of recellularized organs also can be evaluated.

The methods of decellularizing a bone or portion thereof as described herein include perfusing a bone or portion thereof with a physiological buffer under pressure. This perfusion of the decellularized bone or portion thereof under pressure is performed prior to introducing any cells into the decellularized bone or portion thereof, and generally begins with attaching an apparatus to the exogenously introduced aperture(s), e.g., to a cross-section of the central cavity, and applying fluid to that aperture under pressure (about 10 mm Hg to about 2000 Hg). As used herein, perfusion of a bone or portion thereof under pressure refers to delivering a fluid composition (e.g., a physiological buffer) under enough pressure such that substantially all intact cells are removed from the bone or portion thereof. A physiological buffer suitable for pre-cellular perfusion of a decellularized bone or portion thereof under pressure can be any buffer that is compatible with the bone or portion thereof. For example, physiological buffers can include nutrients such as sugars and carbohydrates, and also can include compounds that induce angiogenesis (e.g., VEGF, FGF-1 and/or bFGF). A physiological buffer is generally at physiological pH.

In one embodiment, the physiological buffer suitable for pre-cellular perfusion or cellular perfusion includes but is not limited to phosphate buffer saline (PBS) or culture media solutions suitable for endothelial cell culture including but not limited to EGM-2, EGM-2MV, DMEM, PromoCell Endothelial Cell Medium, Osteoblast growth medium (Alpha MEM), Bone growth medium, Medium 200, DMEMF/12, buffers along with nutritional supplements, e.g., glucose, ascorbic acid, phosphates, dexamethasone, that may be employed for organ perfusion and/or preservation including transplantation.

A population of allogeneic cells or allogeneic cell precursors may be used and prepared from tissue that is allogeneic to that of the recipient and is tested for use by the well-known methods of tissue typing, to closely match the histocompatibility type of the recipient. Most allogeneic approaches will require the use of immunosuppression agents post transplantation.

Controlled System for Decellularizing and/or Recellularizing a Bone or Portion Thereof The invention also provides for a system for decellularizing and/or recellularizing a bone or portion thereof. A bone or a cancellous space within a bone, may be decellularized by perfusing a cellular decellularization medium through the bone. The decellularization agent may be perfused through a cancellous space, a marrow, vessels, or central cavity and/or a cancellous bone compartment. The cellular decellularization medium may be introduced under high pressure to further promote decellularization. An apparatus having a conduit may be utilized to introduce the cellular decellularization medium. The conduit may be sealed, at least in part, to promote accurate and efficient delivery of the cellular decellularization medium.

In certain examples, a hole may be drilled into a central portion of a bone, with the hole extending to or near a target destination, including but not necessarily limited to a cancellous space, the marrow or central cavity, cancellous bone compartment, and/or one or more canals. In an example, the hole is approximately one-quarter inch in diameter. An apparatus having a fitting may be introduced into the hole. The fitting may comprise the conduit or may seat and/or secure the conduit with respect to the hole. The fitting may at least partially seal the hole while providing access to the target destination. The fitting may be secured to the bone and seal the hole to allow the use of relatively high pressure in delivering fluid through the fitting. In an example, the perfusion of approximately 0.5 percent SDS applied with a pressure from approximately two hundred (200) mm Hg to one thousand two hundred (1200) mm Hg may be employed.

A source of cellular decellularization medium and a pump may be fluidly coupled to the fitting and/or conduit to introduce the cellular decellularization medium to the target destination. The pump may be a peristaltic pump that may be configured to deliver a cellular decellularization medium to the target destination at relatively high pressure.

Upon the cellular decellularization medium being introduced into the target destination, the cellular decellularization medium may permeate through the target destination. The permeation may be through existing arterial and/or venous vasculature of the bone. The cellular decellularization medium may subsequently exit the bone via the arterial and/or venous vasculature.

In certain examples, the hole in the central portion of the bone may pass directly through the bone, forming two holes in the surface of the bone. In an example, the bone is a lamellar bone. In an example, the fitting may be positioned with respect to the first hole in the surface of the bone while a plug may be positioned and secured with respect to the second hole in the surface of the bone.

In various examples, the target destination may be accessed, at least in part, by circumferentially cutting through the bone. In one example, the bone is cut proximate to the epiphysis of the bone. The inside of the bone may be reamed or otherwise cleared, at least in part, to provide increased access for the cellular decellularization medium. Direct flow of the cellular decellularization medium may be introduced to the marrow cavity and/or cancellous bone compartment. Direct fluid flow may be utilized to wash out marrow, in an example with the cellular decellularization medium, in alternative examples with fluids other than the cellular decellularization medium.

A fitting may be applied to the cut end of the bone. The fitting may be the same as or physically similar to the fitting placed with respect to the central hole example above. In contrast to the fitting above, which may provide generally orthogonal access to the bone relative to a long axis of the bone, the fitting applied to the end of the bone may provide access to the bone parallel to the long axis of the bone. The fitting may provide at least a partial seal between the target destination and an exterior of the bone while also providing fluid access to the marrow cavity and/or cancellous bone compartment. While the fitting may both secure a conduit and provide at least a partial seal, a bone may be generally cannulated without respect to a cannula being otherwise secured to any structure to provide access for the cellular decellularization medium into the bone.

Rather than an effluent having cell debris exiting primarily or exclusively via arterial and/or venous vasculature of a bone, the epiphysis at each end of the bone may be cut off for ease of flow of cell debris in the effluent through the bone. In various examples, one or more of the cuts are near a femoral head of a bone and a condyle of the bone. The effluent may thereby pass essentially directly through the length of the bone and exit via a circumferential cut.

In various examples, the fitting may include threading configured to secure the fitting to the bone. The fitting may be rotationally inserted into the bone to engage the threading with bone material. Alternative securing mechanisms may be utilized to secure the fitting with respect to the bone and provide at least a partial seal. Such securing mechanisms may include, but are not necessarily limited to, a cable tie, a tube clamp, a worm gear clamp, a quick clamp, or a band such as a tight band. Some of such alternative securing mechanisms may be utilized to secure a bellows or sleeve of a fitting to an exterior of the bone.

Certain examples of the fitting which may be provided in the various examples detailed above may provide for the use of different pressure zones. The different pressure zones may be provided outside of the bone. In an example, a pair of coaxial barriers or sleeves secured with respect to the bone may provide for two coaxial pressure zones. In such an example, the interior pressure zone may be low pressure while the exterior pressure zone may be high pressure. In such an example, the high pressure zone may be substantially coupled to the compact portion of the bone while the low pressure zone may be substantially coupled to a soft or cancellous space within the bone.

In an alternative example, the coaxial barriers or sleeves may create coaxial pressure zones with a vacuum in the exterior pressure zone and a high pressure zone in the interior pressure zone. In such an example, the vacuum may be substantially applied to the compact portion of the bone while the high pressure zone may be substantially applied to the soft or cancellous space within the bone. In an example, the high pressure zone may be coupled to the soft or cancellous space via a fitting secured with respect to the bone. The fitting may be the same or similar to fittings described above.

In one embodiment, a bone or a portion thereof is fitted for NPT threads, which are employed for fluid applications and may require the use of sealing compounds like Teflon tape, to provide the seal. In one embodiment, a bone or a portion thereof is fitted for NPTF threads, e.g., NPTF Dryseal threads, which are employed for higher pressure fluid applications and where the mechanical seal is produced by the mating and slight crushing of the threads when the fittings are tightened, e.g., using a wrench. Both NPT and NPTF threads have a ¾" taper over one foot of length, the same pitch diameter at the top of the hole of internal threads or end of the pipe on external threads, and both have the same thread lengths or depths. The major and minor diameters of both threads differ slightly. With NPT threads, after pressure is applied, slight spaces at the major and minor diameters may exist and so a sealing compound may be employed to fill any gaps. Taps are available for both NPT and NPTF threads having the appropriate form to produce each type of thread. Since NPT threaded parts require sealing compounds, an NPTF tap may be employed for NPT applications.

In one embodiment, a system of the invention generally includes at least one cannulation device for cannulating a bone or a portion thereof, a perfusion apparatus for perfusing the bone or a portion thereof through the cannula(s), and means (e.g., a containment system) to maintain a sterile environment for the bone or a portion thereof. Cannulation and perfusion are well-known techniques in the art. A cannulation device generally includes size-appropriate hollow tubing for introducing into a central cavity or an exogenously introduced aperture of a bone or a portion thereof. A perfusion apparatus can include a holding container for the liquid (e.g., a cellular disruption medium) and a mechanism for moving the liquid through the bone or portion thereof (e.g., a pump, air pressure, gravity, hydraulic cylinder) via the one or more cannulae. The sterility of a bone or portion thereof during decellularization and/or recellularization can be maintained using a variety of techniques known in the art such as controlling and filtering the air flow and/or perfusing with, for example, antibiotics, anti-fungals or other anti-microbials to prevent the growth of unwanted microorganisms.

A system to decellularize and recellularize a bone or a portion thereof as described herein can possess the ability to monitor certain perfusion characteristics (e.g., pressure, volume, flow pattern, temperature, gases, pH and the like). The effectiveness of perfusion can be evaluated in the effluent and in tissue sections. Perfusion volume, flow pattern, temperature, partial $O_2$ and $CO_2$ pressures, solute containing DNA, and pH can be monitored using standard methods.

Sensors can be used to monitor the system. For example, sensors can be used to monitor the pressure of a liquid moving through a cannulated bone or portion thereof; the ambient temperature in the system and/or the temperature of the bone or portion thereof; the pH and/or the rate of flow of a liquid moving through the cannulated bone or a portion thereof; and/or the biological activity of a recellularizing bone or a portion thereof. In addition to having sensors for monitoring such features, a system for decellularizing and/or recellularizing a bone or a portion thereof also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, and/or a compliance chamber. To help ensure stable conditions (e.g., temperature), the chambers, reservoirs and tubing can be water-jacketed.

A system for generating a bone or a portion thereof can be controlled by a computer-readable storage medium in combination with a programmable processor (e.g., a computer-readable storage medium as used herein has instructions stored thereon for causing a programmable processor to perform particular steps). For example, such a storage medium, in combination with a programmable processor, can receive and process information from one or more of the sensors. Such a storage medium in conjunction with a programmable processor also can transmit information and instructions back to the bioreactor and/or the bone or a portion thereof.

A bone or a portion thereof undergoing recellularization can be monitored for biological activity. The biological activity of the cells attached to the bone or a portion thereof can be monitored, for example, for cell division, metabolism, cell viability, new collagen formation and/or new mineral formation. See, for example, *Laboratory Textbook of Anatomy and Physiology* (2001, Wood, Prentice Hall) and *Current Protocols in Cell Biology* (2001, Bonifacino et al., Eds, John Wiley & Sons). In one embodiment, the weight of a bone or a portion thereof can be entered into a computer-readable storage medium as described herein, which, in combination with a programmable processor, can calculate exposure times and perfusion pressures. Such a storage medium can record pre-load and afterload (the pressure before and after perfusion, respectively) and the rate of flow. In this embodiment, for example, a computer-readable storage medium in combination with a programmable processor can adjust the perfusion pressure, the direction of perfusion, and/or the type of perfusion solution via one or more pumps and/or valve controls.

Further Exemplary Decellularization Apparatus and System

The invention provides a decellularization apparatus comprising: a decellularization chamber; a decellularization composition reservoir; a bone or a portion thereof ingress conduit connected to the decellularization composition reservoir and structured to engage and deliver a decellularization composition directly into the bone or a portion thereof; and optionally a bone or a portion thereof egress conduit comprising a conduit engagement structure. In one embodiment, the ingress conduit comprises a conduit structure adapted to engage at least the central cavity. The decellularization chamber can further comprise a bone or a portion thereof positioning structure. The decellularization apparatus is structured to 1) cooperate with and utilize the conduits introduced to the bone or a portion thereof for delivery of a decellularization composition throughout the organ or tissue; and 2) reduce and minimize residency of the decellularization composition on the bone or a portion thereof. One aspect of the decellularization apparatus and system of the invention is that decellularization of the bone or a portion thereof and creation of the scaffold is achieved in the absence of both mechanical disruption and immersion techniques. The components of the decellularization apparatus collectively accommodate and cooperate with natural bone or a portion thereof conduits and/or vasculature, e.g., arteries, arterioles, veins, canals and the like, to deliver and effectuate of the decellularization process.

In one embodiment, the decellularization apparatus is constructed to perform the process while maintaining an aseptic or sterile environment associated with the bone or a portion thereof within the chamber. In one embodiment, the decellularization apparatus includes a decellularization chamber that can comprise a sealed chamber that is structured to position the bone or a portion thereof during decellularization so as to reduce and minimize residency time of excess decellularization composition and separate cellular debris from the bone or a portion thereof.

The decellularization composition can be initially stored within a decellularization composition reservoir for subsequent delivery to the bone or a portion thereof within the decellularization chamber. The decellularization composition reservoir can be composed of any suitable material that can partake in sterile conditioning. The decellularization reservoir can be constructed with dimensions sufficient to contain the desired volume of decellularization composition within.

The decellularization composition reservoir can comprise a fluid delivery conduit, i.e., the ingress conduit, to deliver the decellularization composition into the decellularization chamber and directly into the bone or a portion thereof contained within the decellularization chamber. The ingress conduit can comprise a dispensation control mechanism such as a valve, to regulate the amount and rate of decellularization composition flow into the bone or a portion thereof.

In an alternative embodiment, two or more chemically separated decellularization compositions, or two or more chemically separated ingredients in combination to create a decellularization composition, can be simultaneously or sequentially delivered. In this arrangement, two or more decellularization reservoirs can be employed which converge into a shared unitary fluid delivery conduit.

The components of the decellularization apparatus, e.g., fluid conduits and chambers, reservoirs, can be composed of any suitable material that can be sterilized or partake in sterile conditions and perform the function for that component. Suitable materials for the reservoir containment and decellularization chamber include, but are not limited to, glass and polymeric materials including plastics. Examples of suitable materials include medical grade glass, plastics and polymeric materials, metallic and metallic alloy materials. Materials that can be used can be rigid, semi-rigid or elastomeric, flexible and/or pliable. Suitable polymeric materials include, but are not limited to, polyethylene (PE), polytetrafluoroethylene (PTFE), polyethyl ether ketone (PEEK), polyvinyl chloridine (PVC), polypropylene (PP), polycarbonate, polysulfone, silicone rubber, and the like. The various components of the apparatus can also be coated or treated to enhance their performance or afford properties as might be desired. The various components can be manufactured using conventional techniques and equipment readily available to those in the medical device field, such as thermoplastic or injection molding techniques and equipment.

Residing within the decellularization chamber is the bone or a portion thereof. The interior environment of the decellularization chamber may be sterilized and the chamber containment may be sealed. The entry point of the ingress conduit, and if present the exit point of the egress conduit, should be constructed so as to form an airtight seal associated with the relative juncture point(s) into the decellularization chamber. In one embodiment, the juncture of the ingress conduit into the decellularization chamber and the juncture of the optional egress conduit exiting the decellularization chamber can comprise an elastomeric gasket seal to hermetically seal the exterior environment from the sterile interior environment.

Access into the decellularization chamber can be accomplished by various structures which permit both access and encasement of the contents within the chamber. A variety of suitable structures can be used provided they permit the formation of an airtight seal when closed. Examples include, but are not limited to, lids, hatches, and the like.

The interior construction of the decellularization chamber can comprise a bone or a portion thereof positioning structure. The positioning structure can vary in design, configuration and material according to the specific nature and attributes of the particular bone or a portion thereof to be decellularized. The positioning structure may be constructed to 1) closely replicate and mimic the natural anatomical orientation and suspension of the bone or a portion thereof during both the decellularization and recellularization processes; 2) accommodate the natural geometry and integrity of the bone or a portion thereof; and avoid biological or chemical incompatibility with subsequent recellularization, cell deposition and growth. In one embodiment, the positioning structure further affords the ability to permit sterile maneuvering of the bone or a portion thereof In addition to the interior environment being sterile, the atmospheric conditions are also significant. Suitable temperature, pressure and humidity conditions to optimize preservation of the scaffold should be used. Temperatures for the chamber interior can be from about ambient temperature (22 degrees Celsius) to about 40 degrees Celsius, preferably from about body temperature (37 degrees Celsius) to about 40 degrees Celsius. Conventional and readily available equipment can be used to maintain environmental conditions within the decellularization chamber.

The egress conduit permits transport and removal of excess decellularization composition as well as cellular debris from the bone and interior chamber environment. The egress conduit can further comprise secondary or additional componentry as might be desired. For instance, the egress fluid pathway can include one or more output fluid sampling devices, measuring or monitoring devices, fluid movement components (e.g., pumps), and the like.

The terminal end of the ingress conduit may include a structure that engages and accommodates the aperture used for the delivery point of the decellularization composition into the bone or a portion thereof The conduit engagement structure can take a variety of forms and materials. Such structures can comprise modified conduit terminal ends, such as reduced cross-sectional diameter or tapered diameter ends or end portions dimensioned for insertion into the aperture. One conduit engagement structure can be in the form of threading on a fitting. Another embodiment can be in the form of an adapter, insert, segment or sleeve that couples to the aperture. Another embodiment of a conduit engagement structure can be constructed as a flexible tubular extension of the conduit for insertion into the aperture.

In one embodiment, the conduit engagement structure creates a fluid tight "seal." As a further modification, adjacent the terminal end of the radially expanded end can be a circumscribing groove so as to facilitate placement of a clamp or tie and prevent or reduce the likelihood of slippage and/or leaking.

A wide variety of material(s) for the positioning structure and conduit engagement structure of the apparatus can be employed provided the material(s) are sterilizable and possess the desired structural integrity to perform the function within the apparatus. Examples of suitable materials include glass, plastics and polymeric materials, metals and metallic alloy materials. Materials that can be used can be rigid, semi-rigid or elastomeric, flexible and/or pliable. Suitable polymeric materials include, but are not limited to, polyethylene (PE), polytetrafluoroethylene (PTFE), polyethyl ether ketone (PEEK), polyvinyl chloridine (PVC), Polypropylene (PP), polycarbonate, polysulfone, silicone rubber, and the like. The various components of the apparatus can also be coated or treated to enhance their performance or afford properties as might be desired.

Fluid flow, rate and pressure of the decellularization apparatus can be regulated and controlled passively by orienting the reservoir relative to the chamber in a manner permitting gravitational fluid flow. Alternatively, fluid flow and pressure can be regulated actively by one or more valves, pumps, or other control structures positioned at one or more points within the apparatus circuit. Flow rate, pressure, temperature and duration parameters can vary and be adjusted according to particular requirements and attributes. Pumps can be selected, controlled and/or positioned to provide variable or fixed rates, pulsatile or non-pulsatile flow, active ingress with passive egress, or passive ingress and active egress.

Suitable decellularization process duration can occur between a period from between about 2 hours and about 100 hours or longer, and may include washing, can range from about 12 hours to about 96 hours or longer. Decellularization process time and temperature can be affected by numerous factors, such as age, size, condition, density, surface area, and weight of the bone or a portion thereof, and supplemental techniques.

The invention will be further described in the following examples, which do not limit the scope of the methods and compositions of matter described in the claims.

EXAMPLES

Example 1

A 0.242 inch hole was drilled in the diaphysis of a porcine femur to facilitate the tapping and placement of a ⅛" national pipe thread (NPT) tapered fitting. A ⅛" ID tube was then connected to the fitting, and the bone was placed into 10 liters of 0.5% SDS solution and perfused at a constant pressure of 600 mmHg for 60 hours. Solutions were changed every 6-12 hours and allowed to recirculate between fluid changes. Pressure was maintained via a controlled system utilizing a pressure sensor and an automated voltage feedback loop to control the pump speed. During the 60 hours, the flow rate varied from 1.0-60 mL/min. Decellularization was evident by the active egress (exiting) of cellular material through the native bone vasculature.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of decellularizing a native mammalian bone having cells, comprising:
   a) providing a native mammalian bone having cells and a central cavity, that is modified to include at least one exogenously introduced aperture that extends from the exterior of the bone into the central cavity, in which the aperture is fitted with an apparatus that provides a water tight seal and one or more conduits; and
   b) introducing a cellular disruption medium via at least one conduit of the apparatus through the aperture into the cavity of the bone, wherein the medium is perfused through the aperture under a pressure of at least 200 mm Hg or up to about 2000 mm Hg so as to provide for decellularization of the bone.

2. The method of claim 1 wherein the bone is a human bone.

3. The method of claim 1 wherein the bone is a long bone.

4. The method of claim 1 wherein the conduit is tubing, bellows, cannula or catheter.

5. The method of claim 1 wherein the pressure is about 300 mm Hg to about 2000 mm Hg.

6. The method of claim 1 wherein the pressure is a controlled pressure.

7. A method of decellularizing a portion of a mammalian bone having cells, comprising:
   a) providing a portion of a mammalian bone having cells, which portion has a native end and a transverse end which is fitted with an apparatus that provides a water tight seal and one or more conduits; and
   b) perfusing a cellular disruption medium via the at least one conduit of the apparatus into at least the interior of the portion of the bone under pressure of at least 200 mm Hg or up to about 2000 mm Hg so as to provide for decellularization of the portion of the bone.

8. The method of claim 7 wherein the bone is a human bone.

9. The method of claim 7 wherein the bone is a long bone.

10. The method of claim 7 wherein the apparatus comprises a sleeve which is fitted to the outer circumference of the bone.

11. The method of claim 7 wherein one conduit has a diameter configured to correspond to the central cavity.

12. The method of claim 7 wherein the apparatus comprises at least two conduits.

13. The method of claim 12 wherein the first conduit has a diameter configured to correspond to the central cavity and the second conduit provides for fluid flow into the cortical bone.

14. The method of claim 7 wherein the pressure includes applying a pressure gradient.

15. The method of claim 7 wherein the pressure is about 300 mm Hg to about 2000 mm Hg.

16. The method of claim 7 wherein the portion includes an epiphysis or a diaphysis.

17. A method of decellularizing a portion of a mammalian bone having cells, comprising:
   a) providing a portion of a mammalian bone having cells, which portion has two transverse ends, one of which is fitted with an apparatus that provides a water tight seal and one or more conduits and the other of which provides for a water tight seal; and
   b) perfusing a cellular disruption medium into at least the central cavity of the portion of the bone via the at least one conduit of the apparatus under pressure of at least 200 mm Hg up to about 2000 mm Hg so as to provide for decellularization of the portion of the bone.

18. The method of claim 17 wherein the apparatus comprises a sleeve which is fitted to the outer circumference of the bone.

19. The method of claim 1 wherein the pressure is about 200 mm Hg to about 1000 mm Hg.

20. The method of claim 7 wherein the pressure is about 200 mm Hg to about 1000 mm Hg.

21. The method of claim 1 or 7 wherein the pressure is at least about 300 mm Hg.

\* \* \* \* \*